United States Patent
McNair

(10) Patent No.: US 11,817,186 B1
(45) Date of Patent: *Nov. 14, 2023

(54) MARKER SCREENING AND SIGNAL DETECTION

(71) Applicant: CERNER INNOVATION, INC., North Kansas City, MO (US)

(72) Inventor: Douglas S. McNair, Seattle, WA (US)

(73) Assignee: CERNER INNOVATION, INC., Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,961

(22) Filed: May 18, 2022

Related U.S. Application Data

(63) Continuation of application No. 15/008,439, filed on Jan. 27, 2016, now Pat. No. 11,380,440, which is a continuation-in-part of application No. 13/616,235, filed on Sep. 14, 2012, now abandoned.

(60) Provisional application No. 62/107,952, filed on Jan. 26, 2015, provisional application No. 61/534,729, filed on Sep. 14, 2011.

(51) Int. Cl.
  *G16H 50/20* (2018.01)
  *G16B 20/00* (2019.01)
  *G16H 10/60* (2018.01)

(52) U.S. Cl.
  CPC ............. *G16H 50/20* (2018.01); *G16B 20/00* (2019.02); *G16H 10/60* (2018.01)

(58) Field of Classification Search
  None
  See application file for complete search history.

(56) References Cited

U.S. PATENT DOCUMENTS

| | | |
|---|---|---|
| 6,000,828 A | 12/1999 | Leet |
| 6,778,994 B2 | 8/2004 | Gogolak |
| 7,418,478 B1 * | 8/2008 | Orling ..................... H04L 43/00 709/224 |
| 7,461,006 B2 | 12/2008 | Gogolak |

(Continued)

OTHER PUBLICATIONS

Soden et al., "Effectiveness of exome and genome sequencing guided by acuity of illness for diagnosis of neurodevelopmental disorders", Science Translational Medicine, vol. 6, Issue 265, retrieved from <http://stm.sciencemag.org/content/6/265/265ra 168.full.html>, Dec. 3, 2014, 14 pages.

(Continued)

*Primary Examiner* — Robert W Morgan
*Assistant Examiner* — Edward B Winston, III
(74) *Attorney, Agent, or Firm* — Kilpatrick Townsend & Stockton LLP

(57) ABSTRACT

Systems, methods and computer-readable media are provided for facilitating patient health care through automatic discovery, establishment, and statistical validation of diagnostic-signals in repositories of EMR information, identifying phenotypic diagnostic signals regarding markers or combinations or sequences of patient attributes. Some methods include identifying a first group of patients that have one or more markers and extracting one or more diagnostic statuses that pertain to the whole genome sequencing (WGS) or whole exome sequencing (WES). Statistically significant differences involving frequent itemsets are identified and may be used to evaluate membership of an individual in a class indicative of potential diagnosis via WGS or WES.

20 Claims, 15 Drawing Sheets

(56) References Cited

U.S. PATENT DOCUMENTS

| | | |
|---|---|---|
| 7,650,262 B2 | 1/2010 | Pearson et al. |
| 7,856,362 B2 | 12/2010 | Walker |
| 7,917,374 B2 | 3/2011 | Walker |
| 7,966,196 B2 | 6/2011 | Walker |
| 7,979,373 B2 | 7/2011 | Gogolak |
| 10,431,336 B1 | 10/2019 | Murrish et al. |
| 11,380,440 B1 | 7/2022 | Mcnair |
| 2002/0165852 A1 | 11/2002 | Gogolak |
| 2005/0050077 A1 | 3/2005 | Li et al. |
| 2006/0111847 A1 | 5/2006 | Pearson et al. |
| 2006/0235727 A1 | 10/2006 | Singer et al. |
| 2007/0294113 A1* | 12/2007 | Settimi .................. G16B 50/00 705/3 |
| 2008/0091471 A1 | 4/2008 | Michon et al. |
| 2008/0215402 A1 | 9/2008 | Pearson et al. |
| 2008/0228043 A1* | 9/2008 | Kenedy .................. G16B 20/00 600/300 |
| 2008/0233574 A1* | 9/2008 | Castonguay ......... C12Q 1/6809 435/440 |
| 2008/0305962 A1 | 12/2008 | Wirtz |
| 2009/0055378 A1 | 2/2009 | Alecu et al. |
| 2009/0299645 A1* | 12/2009 | Colby .................... G16B 20/10 506/7 |
| 2009/0326985 A1 | 12/2009 | Martin et al. |
| 2010/0169108 A1 | 7/2010 | Karkanias et al. |
| 2011/0104062 A1 | 5/2011 | Desouza et al. |
| 2013/0185096 A1* | 7/2013 | Giusti .................... G06Q 10/10 705/3 |
| 2013/0231404 A1* | 9/2013 | Segal ..................... G16B 20/20 514/789 |
| 2013/0238359 A1 | 9/2013 | Carter et al. |
| 2014/0222349 A1* | 8/2014 | Higgins ................. G16B 20/00 702/19 |
| 2014/0342919 A1* | 11/2014 | Seddon ................ C12Q 1/6883 506/9 |
| 2014/0379379 A1* | 12/2014 | Janevski ................ G16H 50/20 705/3 |
| 2015/0017636 A1* | 1/2015 | Prichard ............... C12Q 1/6888 435/6.11 |
| 2015/0073719 A1* | 3/2015 | Glynias .............. G01N 33/5308 702/19 |
| 2015/0088870 A1* | 3/2015 | Jayasundera ....... G06F 16/5838 707/723 |
| 2015/0205690 A1* | 7/2015 | Seto ..................... G06F 11/3452 702/182 |

OTHER PUBLICATIONS

Soden et al., "Supplementary Materials for "Effectiveness of exome and genome sequencing guided by acuity of illness for diagnosis of neurodevelopmental disorders"", Science Translational Medicine, vol. 6, Issue 265, retrieved from <http://stm.sciencemag.org/content/suppl/2014/12101/6.265.265ra168.DC1.html>, Dec. 3, 2014, 14 pages.

U.S. Appl. No. 15/671,939, "Final Office Action", dated Mar. 16, 2023, 13 pages.

* cited by examiner $$P(q|x) = P(q)\frac{P(x_1|q)}{P(x_1)}\frac{P(x_2|q)}{P(x_2)}\cdots\frac{P(x_n|q)}{P(x_n)}$$

| | MEDICATION OR COMBO OR CONCOMITANT MEDS | RECEIVED MED OR COMBO (% OF TOTAL) | ACTUAL NBR DIED (% RCVD) | EXPECTED NBR DIED | RELATIVE RISK | ACT/EXP | P-VALUE** | NNH |
|---|---|---|---|---|---|---|---|---|
| 401 | CIPROFLOXACIN | 386 (5.8%) | 129 (33.4%) | 28.3 | 5.9 | 4.6 | <0.0001 | 3.1 |
| 402 | AMIODARONE +PHENYTOIN | 39 (0.6%) | 13 (33.3%) | 3.7 | 5.9 | 3.5 | <0.0002 | 3.6 |
| | IBUPROFEN +AZITHROMYCIN | 25 (0.4%) | 7 (28.0%) | 2.2 | 4.9 | 3.1 | <0.01 | 4.5 |
| | IBUPROFEN +CIPROFLOXACIN | 24 (0.4%) | 6 (25.0%) | 2.5 | 4.4 | 2.4 | <0.05 | 5.2 |
| | VALPROIC ACID | 53 (0.8%) | 12 (22.6%) | 4.8 | 4.0 | 2.5 | <0.004 | 5.8 |
| | AMIODARONE +LEVOFLOXACIN | 277 (4.1%) | 49 (17.7%) | 26.5 | 3.1 | 1.8 | <0.0001 | 8.0 |
| | ACETAMINOPHEN +PHENYTOIN | 135 (2.0%) | 24 (17.8%) | 8.5 | 3.1 | 2.8 | <0.0001 | 8.1 |
| | PHENYTOIN | 158 (2.4%) | 27 (17.1%) | 9.7 | 3.0 | 2.8 | <0.0001 | 8.6 |
| | AMIODARONE +AZITHROMYCIN | 65 (1.0%) | 9 (13.8%) | 4.6 | 2.4 | 1.9 | <0.05 | 12.1 |
| | ACETAMINOPHEN +AZITHROMYCIN | 277 (4.1%) | 31 (11.2%) | 18.0 | 2.0 | 1.7 | <0.003 | 17.4 |
| | LEVOFLOXACIN | 736 (11.0%) | 79 (10.7%) | 51.4 | 1.9 | 1.5 | <0.0001 | 17.6 |
| | AZITHROMYCIN | 327 (4.9%) | 33 (10.1%) | 20.8 | 1.8 | 1.6 | <0.006 | 21.5 |
| | ONDANSETRON +CIPROFLOXACIN | 245 (3.7%) | 24 (9.8%) | 16.6 | 1.7 | 1.4 | <0.0001 | 23.4 |
| | FLUOXETINE | 131 (2.0%) | 11 (8.4%) | 4.9 | 1.5 | 2.2 | <0.02 | 36.0 |
| 403 | ENTIRE COHORT | 6,699 (100%) | 380* (5.7%) | N/A | 1.0 | N/A | N/A | N/A |

FIG. 4A.

| MEDICATION OR COMBO OR CONCOMITANT MEDS | RECEIVED MED OR COMBO (% OF TOTAL) | ACTUAL NBR GR.4 LIVER INJ (% RCVD) | EXPECTED NBR GR. 4 LIVER INJ | RELATIVE RISK | ACT/EXP | P-VALUE | NNH |
|---|---|---|---|---|---|---|---|
| IBUPROFEN +LEVOFLOXACIN | 58 (0.9%) | 9 (15.5%) | 3.5 | 5.3 | 2.5 | <0.02 | 7.8 |
| AMIODARONE +LEVOFLOXACIN | 277 (4.1%) | 35 (12.6%) | 18.1 | 4.3 | 1.9 | <0.0003 | 9.8 |
| AMIODARONE +IBUPROFEN | 110 (1.6%) | 12 (10.9%) | 5.8 | 3.8 | 2.1 | <0.02 | 12.2 |
| LEVOFLOXACIN | 736 (11.0%) | 54 (7.3%) | 35.7 | 2.5 | 1.5 | <0.001 | 19.9 |
| ONDANSETRON +LEVOFLOXACIN | 439 (6.6%) | 32 (7.3%) | 20.4 | 2.5 | 1.6 | <0.01 | 21.1 |
| VENLAFAXINE | 111 (1.7%) | 8 (7.2%) | 3.6 | 2.5 | 2.2 | <0.04 | 22.7 |
| ENTIRE COHORT | 6,699 (100%) | 192 (2.9%) | N/A | 1.0 | N/A | N/A | N/A |

FIG. 4B.

| | Drug(s) | Nbr Received Med or Combo | Exposure Prev. | AE1 (In-House Mort) | | AE2 (Gr-1) | AE3 (Gr-2) | AE4 (Gr-3) | AE5 (Gr-4) | Hep Tox % |
|---|---|---|---|---|---|---|---|---|---|---|
| 1 | acetaminophen | 5120 | 76.4% | 263 | 5.1% | 1798 | 818 | 526 | 147 | 2.9% |
| 2 | allopurinol | 149 | 2.2% | 6 | 4.0% | 57 | 21 | 11 | 7 | 4.7% |
| 3 | amiodarone | 1496 | 22.3% | 129 | 8.6% | 599 | 338 | 253 | 70 | 4.7% |
| 4 | amlodipine | 893 | 13.3% | 44 | 4.9% | 297 | 111 | 64 | 18 | 2.0% |
| 5 | atorvastatin | 2391 | 35.7% | 81 | 3.4% | 822 | 389 | 258 | 48 | 2.0% |
| 6 | azithromycin | 327 | 4.9% | 33 | 10.1% | 159 | 71 | 44 | 17 | 5.2% |
| 7 | captopril | 168 | 2.5% | 8 | 4.8% | 71 | 41 | 33 | 10 | 6.0% |
| 8 | carbamazepine | 27 | 0.4% | 2 | 7.4% | 10 | 4 | 2 | 1 | 3.7% |
| 9 | chlorpromazine | 41 | 0.6% | 2 | 4.9% | 17 | 15 | 5 | 2 | 4.9% |
| 10 | ciprofloxacin | 386 | 5.8% | 52 | 13.5% | 203 | 92 | 69 | 26 | 6.7% |

EXAMPLE POPULATION: AMI IN-PATIENTS BETWEEN 35 AND 60 YEARS OLD (ADM IN 2008-2010 WITH LOS > 3D AND LFTS > 0)
TOTAL POPULATION = 6699
TOTAL NUMBER DIED = 380 (5.7%)
NUMBER WITH GRADE-4 LIVER FAILURE = 192 (2.9%)

*FIG. 5A.* TO 5B. ➡

| | POP-EXPOSED 560 | MORTALITY 570 | | | | | | GR-4 LIVER INJURY 580 | | | | | | 596 | 598 |
|---|---|---|---|---|---|---|---|---|---|---|---|---|---|---|---|
| | EXPNEG TOT | EXPPOS POS | EXPPOS NEG | EXPNEG POS | EXPNEG NEG | NNT1 | NNH1 | EXPPOS POS | EXPPOS NEG | EXPNEG POS | EXPNEG NEG | NNT2 | NNH2 | NNT1/NNH2 | NNT2/NNH1 |
| 1 | 1579 | 263 | 4857 | 117 | 1462 | 44.0 | | 147 | 4973 | 45 | 1534 | | 4720 | 0.0 | |
| 2 | 6550 | 6 | 143 | 374 | 6176 | 59.4 | | 7 | 142 | 185 | 6365 | | 53.4 | 1.1 | |
| 3 | 5203 | 129 | 1367 | 251 | 4952 | | 26.3 | 70 | 1426 | 122 | 5081 | | 42.8 | | |
| 4 | 5806 | 44 | 849 | 336 | 5470 | 116.3 | | 18 | 875 | 174 | 5632 | 101.9 | | | |
| 5 | 4308 | 81 | 2310 | 299 | 4009 | 28.1 | | 48 | 2343 | 144 | 4164 | 74.9 | | | |
| 6 | 6372 | 33 | 294 | 347 | 6025 | | 21.5 | 17 | 310 | 175 | 6197 | | 40.8 | | |
| 7 | 6531 | 8 | 160 | 372 | 6159 | 107.1 | | 10 | 158 | 182 | 6349 | | 31.6 | 3.4 | |
| 8 | 6672 | 2 | 25 | 378 | 6294 | | 57.4 | 1 | 26 | 191 | 6481 | | 118.9 | | |
| 9 | 6658 | 2 | 39 | 378 | 6280 | 125.1 | | 2 | 39 | 190 | 6468 | | 49.4 | 2.5 | |
| 10 | 6313 | 52 | 334 | 328 | 5985 | | 12.1 | 26 | 360 | 166 | 6147 | | 24.4 | | |

| couple_guid; marker_cki; dx_cki; n11 |
|---|
| 175;M_1;DX_175;1 |
| 224;M_1;DX_224;1 |
| 225;M_1;DX_225;1 |
| 233;M_1;DX_233;1 |
| 256;M_1;DX_256;1 |
| 465;M_1;DX_465;1 |
| 508;M_1;DX_508;1 |
| 550;M_1;DX_550;1 |
| 551;M_1;DX_551;1 |
| 565;M_1;DX_565;1 |
| 622;M_1;DX_622;1 |
| 653;M_1;DX_653;1 |
| 663;M_1;DX_663;1 |
| 694;M_1;DX_694;1 |
| 724;M_1;DX_724;1 |
| 761;M_2;DX_5;1 |
| 769;M_2;DX_13;1 |
| 778;M_2;DX_22;1 |
| 789;M_2;DX_33;1 |
| 791;M_2;DX_35;12 |
| 797;M_2;DX_41;2 |
| 805;M_2;DX_49;5 |
| 843;M_2;DX_87;4 |
| 844;M_2;DX_88;1 |
| 849;M_2;DX_93;1 |
| 860;M_2;DX_104;2 |
| ⋮ |

FIG. 5C.

```
# CERDSM - predictors of next-gen genomics exome sequencing diagnostic yield          600

# source("http://bioconductor.org/biocLite.R")
# biocLite("LBE")
library(LBE)
library(coda)
library(lattice)
library(MASS)
library(MCMCpack)
library(PhViD)
library(arules)
library(arulesNBMiner)

# load transactions table containing patterns of phenotypic markers and counts
wes.pat <- random.patterns(1000, nPats=2000, method="agrawal", lPats=2, corr=0.3, cmean=0.5, cvar=0.2,
iWeight=NULL, verbose=FALSE)
wes.db <- random.transactions(1000, 102483, method="agrawal", patterns=wes.pat)

# perform association rule mining using Negative Binomial distribution for marker itemset counts
wes.param <- NBMinerParameters(wes.db, pi=0.99, theta=0.5, maxlen=5, minlen=1, trim=0.14, verb=TRUE,
plot=TRUE)
itemsets <- NBMiner(wes.db, parameter=wes.param, control=list(verb=TRUE, debug=FALSE))
itemsets@items@itemInfo$labels <- paste0("M_",1:1000)

# load table containing 1-set and N-set phenotypic markers, genomics sequencing-yielded diagnoses, and counts.
# PhViD expects to process a .csv file which must have ";" as column separator.
# first two columns must be the marker and the diagnosis in each marker-dx couple.
# third column is the number of occurrences of the marker-dx couple.
# example has 634 phenotypic markers and 756 diagnoses resulting from whole exome sequencing (WES).
# of the 479,304 pairwise combinations that are possible, only 102,483 (21.4%) yield non-NULL diagnoses via WES.
wes <- read.csv(file="c:/0_cerdsm/0__math_models/genomics_screening_of_kids/wes.csv", header=TRUE,
       colClasses=c("integer", "factor", "factor", "integer"), sep=";", quote="\"")

# transform raw data to [n11, n1., n.1] array for signal detection
wesx <- as.PhViD(wes[,-1])

# perform signal detection (Note that marker is analogous to 'drug' and diagnosis is analogous to 'AE'.)
# calculate Bayesian Confidence-propagation Neural Network (BCPNN) signal
wes1 <- BCPNN(wesx, RR0=1, MIN.n11=1, DECISION=3, DECISION.THRES=2, RANKSTAT=2, MC=TRUE, NB.MC=10000)
colnames(wes1$SIGNALS) <- c("marker_cki","dx_cki","n11_count","exp_count","Q_0.025_logIC","n11_exp_ratio",
           "marker_margin","dx_margin","FDR","FNR","Se","Sp","postH0")
write.csv(wes1$SIGNALS, file="c:/0_cerdsm/0__math_models/genomics_screening_of_kids/wes_bcpnn.csv")
349 rows calculate Multi-item Gamma-Poisson Shrinker (MGPS) signal
wes2 <- GPS(wesx, RR0=1, MIN.n11=1, DECISION=3, DECISION.THRES=2, RANKSTAT=2, TRONC=FALSE,
TRONC.THRES=1,
       PRIOR.INIT=c(alpha1=0.2, beta1=0.06, alpha2=1.4, beta2=1.8, w=0.1), PRIOR.PARAM=NULL)
colnames(wes2$SIGNALS) <- c("marker_cki","dx_cki","n11_count","exp_count","Q_0.025_logIC","n11_exp_ratio",
           "marker_margin","dx_margin","FDR","FNR","Se","Sp","postH0")
write.csv(wes2$SIGNALS, file="c:/0_cerdsm/0__math_models/genomics_screening_of_kids/wes_mgps.csv")
# 3,540 rows

# optionally apply epidemiologic prevalence multiplier to determine population rank of each marker-dx couple signal
```

*Continues in FIG. 6B*

*FIG. 6.*

MARKER SCREENING AND SIGNAL DETECTION

CROSS REFERENCE TO RELATED APPLICATIONS

This application claims the benefit of U.S. patent application Ser. No. 15/008,439 titled "Marker Screening and Signal Detection," filed Jan. 27, 2016, which claims the benefit of U.S. Provisional Application No. 62/107,952 titled "Marker Screening and Signal Detection," filed Jan. 26, 2015, each of which are hereby expressly incorporated by reference in its entirety. This application is a continuation-in-part application and claims the benefit of U.S. application Ser. No. 13/616,235, titled "Context-Sensitive Health Outcome Surveillance and Signal Detection," filed Sep. 14, 2012, which claims the benefit of U.S. Provisional Application No. 61/534,729, filed Sep. 14, 2011, each of which is hereby expressly incorporated by reference in its entirety.

INTRODUCTION

The progressively diminished cost to perform genetic and genomic testing, including whole genome sequencing (WGS) and whole exome sequencing (WES) is now producing significant clinical benefits for individual patients. Inborn errors of metabolism (IEM) are a phenotypically and genetically heterogeneous group of disorders caused by a defect in a metabolic pathway, leading to malfunctioning metabolism, developmental disorders, and in many cases increased morbidity and mortality. To date, more than 1,000 different IEMs have been identified. While individually rare, the cumulative incidence is upwards of 1 in 800. Clinical presentations of such conditions are protean, an aspect that complicates decision-making to establish an accurate diagnosis. IEM are present in all ethnic groups and across every age, although the majority of testing is currently performed in children. Some IEM are amenable to treatment, with promising outcomes, while others are not responsive to any treatments presently known.

In the health insurance sector, private payers struggle to determine what molecular tests are clinically justified for advancement of personalized medicine, and it is extremely difficult to include cost-effectiveness of molecular testing in their coverage decision-making While the private for-profit laboratories may have coverage arrangements to bill insurance directly, these are 'local coverage decisions' made by different payers, and coverage cannot be assumed. Payers establish their own policies for which specific diagnostic codes justify payment. Uncovered test costs are charged back to the originating provider (typically a hospital), or directly to the patient.

Our health system has created an extraordinary gap in coverage for molecular tests emanating from hospitals during an inpatient admission. If a restrictive license is in place for a patented FDA-approved molecular test, a hospital-based laboratory is prevented from performing the test, despite the fact that gene sequences are known, and a competent hospital-based laboratory could develop and validate the test in-house. The hospital must send out the test to a licensed private, for-profit reference laboratory. The for-profit laboratory can charge the full cost of the molecular test, often in the thousands of dollars, back to the source hospital. The hospital must bear the financial burden of the send-out test, owing to the fact that this testing is part of an episode-of-care declared by the Medicare prospective payment (DRG) system.

The U.S. therefore has a payment system which expects hospitals to cover the costs of expensive send-out molecular tests emanating from patient admissions, without opportunity to recover the costs charged back to the hospital from private, for-profit laboratories. An attempt by the hospital to deny such molecular testing on the premise that the results of such testing have no effect on clinical management decisions made during that hospital stay, is met by considerable resistance from the treating physicians, who rightfully claim that the patient was admitted in order to receive appropriate medical care, including molecular diagnostics for their inherited conditions or cancers.

Although the cost of WGS and WES testing is declining, its cost is nonetheless several thousand dollars. And it is usual that only about 25% of persons tested by WGS or WES are determined to have a specific diagnosis. In the other 75% of persons, the cost of testing is incurred but no useful, actionable information is produced. The proportion of persons tested in whom a specific diagnosis is produced is termed the 'diagnostic yield'. Thus, given that diagnostic yield that is very far from 100%, even screening procedures that have comparatively low cost can be associated with very large aggregate spending and low cost-effectiveness when applied to large populations. Cost-effectiveness analysis is therefore key to sustainable public policy regarding gating criteria for provisioning of such tests.

Accordingly, screening via whole genome sequencing or whole exome sequencing will in general not be cost-effective unless criteria favorable to an acceptably-high positive diagnostic yield of screening tests are adopted. This is necessary in order to meet economic criteria used to determine commercial payor or federal regulatory policies.

SUMMARY

Systems, methods and computer-readable media are provided for facilitating patient health care through the automatic discovery, establishment, and statistical validation of diagnostic signals in repositories of electronic medical record (EMR) information, identifying phenotypic diagnostic signals regarding new or existing markers or combinations or sequences of attributes patients, either in an acute or chronic health care setting or in an ambulatory/home setting. For example, in one embodiment, a database of healthcare claims is utilized and the method includes identifying from the database a group of patients who have one or more markers; extracting one or more diagnostic statuses that pertain to the group of patients tested with diagnostics such as whole genome sequencing (WGS) or whole exome sequencing (WES); determining one or more statistically significant differences involving frequent itemsets comprised of two or more marker combinations that occur concomitantly in members of the group; determining statistical disproportionality signals among the items and itemsets with regard to the likelihood that WGS or WES will yield a specific, actionable diagnosis; and determining membership of an individual in a diagnostic-yield subset of the group according to the individual's manifesting one or more of the identified signals. In some embodiments, the method further includes computing a probability value for each of the one or more common marker itemset occurrences. In this way, embodiments of the invention may be used to identify and quantify the probability that certain diagnostic yield will prevail in patients in whom WGS or WES testing is performed, given a combination of phenotypic markers. Correspondingly, patients in whom WGS or WES testing would be unlikely to yield an actionable diagnostic result are also identified.

BRIEF DESCRIPTION OF THE DRAWINGS

Embodiments of the invention are described in detail below with reference to the attached drawing figures, wherein:

FIG. 4A provides example results from an embodiment of our invention, sometimes referred to herein as Event Surveillance System or DiscernESS (Trademark), showing detection of statistically significant medication combinations that were associated with increased relative risk of in-hospital patient death;

FIG. 4B provides example results of an embodiment showing detection of statistically significant medication combinations that were associated with increased relative risk of developing in-hospital, life-threatening Grade 4 drug-associated liver injury;

FIGS. 5A and 5B illustratively show a portion of results from the application of the embodiment described above in connection to FIGS. 4A and 4B;

FIG. 5C shows a hash table of information including combinations of markers in a patient and corresponding diagnosis of sequence testing for use in predicting markers likely indicative of positive actionable sequence testing diagnoses;

FIG. 6 illustratively provides an example embodiment of a computer program routine for carrying aspects of the methods of FIG. 3A-3C, in accordance with an embodiment of the invention;

DETAILED DESCRIPTION

Figures 1A, 1B:
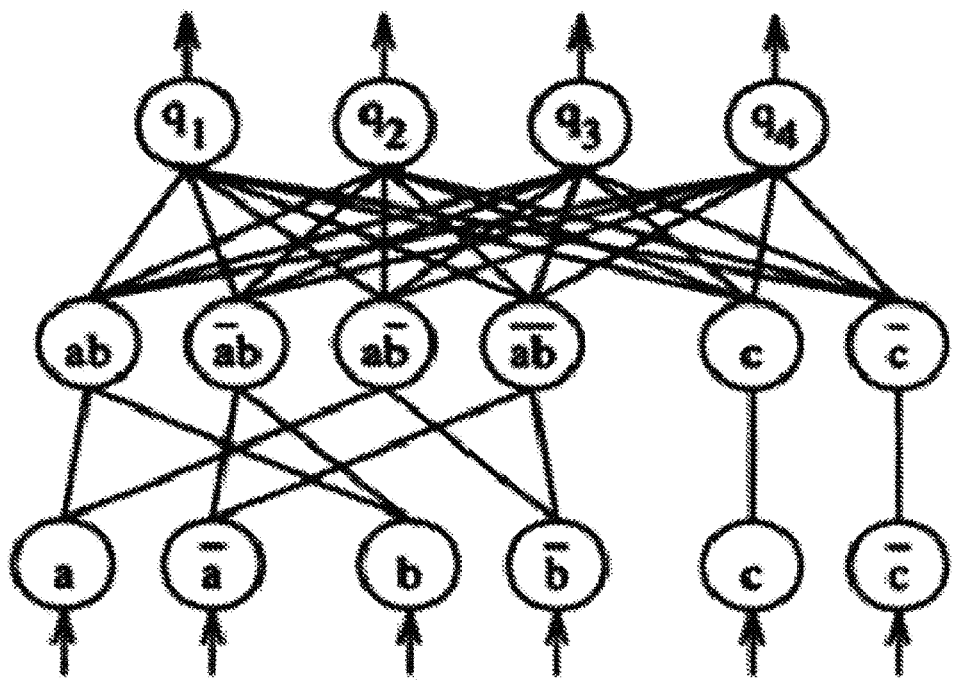
FIG. 1A illustrates an example Bayesian confidence-propagation neural network having one 'complex' or 'compound' column variable (ab) and one simple first-order column variable (c)
FIG. 1B provides an equation of Bayes theorem for the probability of $q_j$ conditioned on x where there is one unit for each outcome of each input variable given as xi (where i is 1 to n) and one unit for each output class qj.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and non-volatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or storage devices. These technologies can store data momentarily, temporarily, or permanently.

As described previously, Embodiments of the invention provide systems and methods for facilitating patient health care through the automatic discovery, establishment, and statistical validation of diagnostic-yield signals and/or safety signals in repositories of electronic medical record (EMR) information. In particular, embodiments of the invention may include identifying phenotypic diagnostic signals regarding new or existing markers or combinations or sequences of attributes patients or identifying safety signals regarding new or existing therapeutics or combinations or sequences of therapeutics administered to patients, either in an acute or chronic health care setting or in an ambulatory/home setting.

With regards to embodiments directed to identifying safety signals, the safety of medications, medical devices, and therapeutic procedures is a matter of great concern worldwide, both to public health agencies and regulators and to health care providers, insurers, and consumers. It is a matter of great economic importance to manufacturers of therapeutic products, insofar as their financial success and sustainability depends on making sure that their products have acceptable safety and do not become the subject of tort litigation or regulator-mandated removal from the market. Increasingly, the safety of therapeutic products is evaluated not only in pivotal clinical trials that form the basis for regulatory approval and market launch, but also in post-market surveillance observational studies. Such studies include registries and Phase IV "open" clinical trials, but also traditionally include statistical analysis of spontaneous adverse event reports that are received by regulatory agencies.

The U.S. Adverse Event Reporting System (AERS) contains over 3 million adverse event reports spontaneously submitted by health care providers, pharmaceutical companies, and the public since 1968. The World Health Organization's Vigibase system likewise contains millions of spontaneous adverse event reports. For coding adverse events, these systems currently utilize the CIOMS Medical Dictionary for Regulatory Activities (MedDRA) classification system with over 15,000 preferred terms (PTs). AERS currently has about 10,000 PTs and 4,000 generic drug names in use. Thus, approximately 43 million drug-event combinations (DECs) are possible in the AERS database.

However, considered as a two-way (drug-by-event) table, the AERS database is quite sparsely populated. Only approximately 2.8 million (0.7%) of approximately 43 million possible DECs have ever been spontaneously reported by humans. A large proportion (67%) of the 2.8 million DECs that have been reported one or more times contain fewer than three reports, and approximately half of the DECs exist only once. The sparseness of spontaneous reports in the AERS and Vigibase and similar databases may arise predominantly from the considerable limitations of human pattern recognition and logistical and sociological factors that inhibit people from preparing and submitting spontaneous adverse event reports. In other words, the sparseness of spontaneous reports is not necessarily evidence of the absence of safety issues for drug-event combinations that have never received spontaneous reports. And, in fact, the sparseness and the skewed frequency distributions of spontaneous reports cause significant limitations in the ability of systems that rely on spontaneous reports to detect safety signals in a sensitive, specific, and timely manner—even for the drug-event combinations that have received some spontaneous report activity.

With regards to embodiments directed to phenotypic diagnostic signals or diagnostic-yield signals, as described previously, even screening procedures that have comparatively low cost can be associated with very large aggregate spending and low cost-effectiveness when applied to large populations. Thus, screening via whole genome sequencing or whole exome sequencing will in general not be cost-effective unless criteria favorable to an acceptably-high positive diagnostic yield of screening tests are adopted.

It is not uncommon for a particular finding (e.g., epicanthal folds) or biomarker (e.g., HLA-B27) to be independently associated with a wide variety of inherited conditions. In principle, one might consider applying a large set of such findings or markers as a means of determining disease acuity, severity, or propensity to yield positive diagnostic results in WGS or WES testing. However, it can be readily shown that, if each finding's positivity is governed by a binomial stochastic process, then as the size of the set of findings grows, the likelihood that every individual will be determined to have at least one abnormal finding approaches 100%. This would thwart the aim of rationally and objectively guiding the provisioning of the comparatively expensive testing to those in whom a useful, actionable, specific result is most likely.

Furthermore, it is an inherent aspect of the observational data that accrues with screening and with subsequent testing that not all marker-diagnosis pairs (dyads or "couples") have non-NULL frequency. Some marker-diagnosis couples may not ever have been encountered in the prevalent patient population that has to-date presented for evaluation. Additionally, the variability of the evaluation process entails that some findings or markers may not have been measured or noticed or are for other reasons NULL or unremarked in the entirety of the extant data.

Yet further, the available data inevitably do not contain balanced representation of the couples with non-NULL counts in the database. In other words, some non-NULL couples that are relatively more common in the population may typically have moderately high cumulative counts, whereas other non-NULL couples that are relatively rare may have only one or a few counts.

Therefore, it is desirable to have a system and method that can discover the strength of association of each particular WES- or WGS-determined diagnosis with members of the set of findings and markers that are available prior to the performance of WES or WGS [Sims 2014]. It is desirable that said system and method be robust against imbalancing among the marker-diagnosis couples represented in the dataset and that the system and method reveal the degree of disproportionality of diagnoses arising with statistically significant couples. In this manner it will be practical to accomodate large sets of findings and markers and large sets of potential diagnoses without devolving into the uneconomic situation of having to perform expensive testing in 100% of the incident population.

Whole genome sequencing (WGS) provides comprehensive collection of genetic variations and thus is promising in discovering novel inheritable factors for both Mendelian and complex traits. Two data properties distinguish WGS from microarray-based genome-wide association study (GWAS). First, WGS data contain rare causal mutations that could have large allelic effect. However, the statistical association for such rare variants is weak at population level because of small allele frequency; therefore, population-based case-control study designs, which are commonly applied in GWAS, are less powerful for WGS. Second, family study designs are attractive and commonly applied in WGS studies. Causal rare variants are likely enriched through co-transmission in families Moreover, pedigree structures allow statistical imputation of genotypes without additional diagnostic testing expense. Additionally, family-based data analyses automatically control for population stratification and are potentially able to incorporate helpful genetic information on phase, effects of parental origin, cotransmission of variants, and so on.

Detection of disease variants can also be facilitated by longitudinal ("trajectory") information on individual changes over time. Longitudinal genetic studies enable a close investigation of both genetic factors that lead to a disease and environmental determinants that modulate the subsequent progression of the disease. In WGS, it can be important to utilize powerful methods that accommodate both within-family correlation structure and correlation among repeated measures.

The comparatively good diagnostic yield of WES supports its use in pediatric neurology practices. It may also lead to earlier diagnosis, impacting medical management of the affected individual and family planning for the parents or immediate family A further consideration is the public health value of screening a number of patients even though pre-screening evaluation predicts that WGS or WES in the patients will not likely yield specific diagnoses. In other words, the continuation of discoveries of new patterns and genomic relationships would be seriously impaired if rationing of sequencing were pursued in an overly-restrictive manner Just as financial sustainability would be jeopardized if testing is undertaken in too many, the long-term value and augmentation of knowledge would be jeopardized if testing is undertaken in too few.

In this regard, there are thousands of attributes or markers that are associated with neurodevelopmental disorders and other inherited conditions to which WES or WGS can be fruitfully applied. By way of example and not limitation, such markers include the following: neuromotor developmental milestone delay, brain ventriculomegaly or hydrocephalus, Chiari malformation, epicanthal folds, upslanted or downslanted palpebral fissures, bitemporal narrowing, ptosis, hypoplasia of supraorbital ridges, Cupid's bowlip, deep philtrum or shallow philtrum, ear anomalies, cortical blindness, short stature, prognathism, high forehead, relative macrocephaly, flattened mid-face, short nose with depressed bridge, anteverted nares, frontal bossing, brachycephaly, hypertelorism, abnormal fingerprints, hypotonia, spasticity, posturing of hands, choreoathetoid movements, atrial or ventricular septal defects, hypoplastic left or right heart syndrome, pulmonic or aortic stenosis, coarctation of the aorta, other abnormality of the great vessels, other cyanotic heart disease, long QT syndrome, digital clubbing, atresia in the GI tract, GI dysmotility and reflux, aspiration, vomiting, constipation, splenomegaly, hepatomegaly, kidney anomalies, autism spectrum signs and symptoms, mood lability, excessive anxiety, aggression, irritability, piercing gaze, stereotypic hand movements (wringing, tapping, clasping, squeezing, finger-rubbing), stereotypic oral movements (air-swallowing, breath-holding, hyperventilating, bruxism), apraxia, wide-based gait, alogia, dyslexia, metopic synostosis, epilepsy, agenesis of corpus callosum, stenosis of sylvian aqueduct, cerebral hamartomas, and cavum septum pellucidum, wide spaces between first and second toes, short neck, failure to thrive, sparse-curly-fine hair, thick, wooly, or brittle hair, absent eyelashes and eyebrows, eczema, xerosis, keratosis pilaris, ichthyosis, pigmented nevi, palmoplantar hyperkeratosis, cafe au lait macules, strabismus, nystagmus, astigmatism, myopia, optic nerve hypoplasia, cortical blindness, scoliosis, kyphosis, osteopenia, pectus deformity, pterygium colli, and various genital abnormalities. Any particular patient may manifest a plurality of features concomitantly. However, it is common that not all of the extant features or markers are noticed simultaneously, even if they are present simultaneously. The most distinctive or severely abnormal markers are usually noticed and recorded first and—through a succession of increasingly detailed examinations over a period of many months, performed by a series of clinicians of progressively greater experience or sub-specialization—a comprehensive set of markers is disclosed and recorded in the electronic health record. Thus, the phenotypic patterns are variable in time, depending on the stage of the diagnostic workup. Any effective system and method for screening markers according to diagnostic-yield must possess a means of accommodating variable markerset length and time-dependence of marker compositions.

Additionally, certain historical findings or trajectory patterns of longitudinal changes in discrete markers may also serve as derived or 'composite' markers (for example, perinatal periventricular hemorrhages, hypoxia, or developmental regression).

Yet further, there are environmental exposures that constitute markers in the sense of being statistically associated, or predisposing-toward, or accelerating the development of, or causing a condition which can be diagnosed via WGS or WES testing (for example, prenatal maternal viral or bacterial infections, or maternal use of tobacco or alcohol or drugs, or maternal industrial solvents or heavy metals exposure, or maternal diabetes or systemic lupus erythematosis).

In this connection, data mining is a potentially useful adjunct to traditional pharmacovigilance and diagnostic methods. The results of data mining should be viewed as an empirical means of signal-detection and hypothesis-generating and should be evaluated in the context of other relevant data. Empirical Bayes (EB) and Multi-item Gamma Poisson Shrinker (MGPS) and the Proportional Reporting Ratio (PRR) methods can be used to classify medication-related adverse events as signals based on the disproportionality of these events in databases and to prioritize the pursuit of other relevant data to assess causality and potential remedies to mitigate safety issues or diagnostic-yield issues that are detected and validated.

Conventionally, aggregate analysis of observational data consists of examining differences in outcome frequency between a group having the exposure of interest, and groups lacking that exposure. But the groups must be similar at 'baseline'. If they are not, then interpretation will have a high rate of false-positive and false-negative errors.

The International Society for Pharmacoepidemiology (ISPE) in its 2004 commentary on FDA Guidance documents specifically cautions against calculating PRR reporting rates using the entire safety database to derive an expected rate, asserting that a more appropriate expected rate is the PRR for comparable chemical entities with similar indications, or at least all drugs with comparable indications to reduce the number of false-positive signals due to the disease being treated or its known and expected complications.

Traditionally, however, signal detection in pharmacovigilance operations does not obey this principle but instead entails pooling all medication exposures and all adverse event types (AEs). However, the patient populations receiving different medication regimens are vastly different with different statistical distributions of diagnoses, disease severity levels, and physiologic reserve (ability to tolerate physiologic stresses and recover from them, with transient abnormalities during the period of challenge reverting to normal after the challenge is removed). The consequence is that pooling all populations and all AE types leads to excessive false-negative rates of signal detection. Analogous phenomena also affect discovery of diagnostic-yield related patterns. The status of diagnostic positivity from WES or WGS sequencing involve observational groups that are assuredly not similar at 'baseline' and whose polygenic and environmental and other factors constitute differences such that pooling would result in an excessive false-negative rate.

Regarding signal detection in pharmacovigilance operations, rather than "all exposures—all AEs," it would be preferable instead to perform safety signal detection by comparing drug-AE incidence rates in a manner that considers "context-sensitive exposures—context-relevant AEs." For example, morphine, acetaminophen, aspirin, atorvastatin, lisinopril, metoprolol, and ondansetron are empirically prescribed in more than 35% of all AMI in-patients and may be considered to be part of contemporary de facto standard of care.

For patients facing serious or life-threatening illness, the goals and objectives of care generally do not permit abating curative or salvific interventions, or eliminating medications that are essential to saving the patient's life, and so forth, even if those curative interventions confer substantial risk of AEs or serious side-effects. The calculus of rational therapy decisions involves balancing benefits against risks. Situations where the risk of acute mortality is 30% or greater can justify utilizing therapeutic options that themselves may carry up to 30% likelihood of serious harm.

EMPIRICALLY BALANCING LIKELY BENEFITS AND RISKS UNDER UNCERTAINTY

Generally, it is not sensible to embark on a therapeutic option where the population-level 'number-needed-to-treat' (NNT) or the individually personalized NNT for the therapeutic benefit substantially exceeds the 'number-needed-to-harm' (NNH) for an AE type that occurs with a substantial frequency (i.e., NNT1/NNH2 >1.0). In terms of principles of evidence-based medicine, the metrics 'number-needed-to-treat' (NNT) and 'number-needed-to-harm' (NNH) are used to assess the balance of probable benefits and harms.

But the 'exposure-negative' row in the 2×2 contingency tables that are used to compute NNT and NNH should contain counts for an alternative intervention that has adequate efficacy for treating the same condition as the counts for the agent in the 'exposure-positive' row reflect. Contrary customary practice, the 'exposure-negative' row should not be filled with counts for cases whose treatment regimen does not address the condition.

An NNT is treatment-specific and describes the difference between a treatment and a control in achieving a particular desirable clinical outcome, such as survival. Similarly, an NNH is treatment-specific and describes the difference between a treatment and a control in causing a particular undesirable clinical outcome, such as liver injury or mortality. It can be used to describe any outcome where event rates are available for both a treatment and a control.

Bayesian confidence-propagation neural network (BCPNN) algorithms are one means by which probabilities for various outcome states or beneficial events and harmful events can be jointly computed from multiple concurrent input variables, where the variables' values may be time-dependent or uncertain.

With reference to FIGS. 1A and 1B, Bayesian confidence-propagation neural networks are designed to calculate the probabilities of some output attributes (classes) from the values of input variables by a computational abstraction involving one or more interconnected "layers." If there is one unit for each outcome of each input variable xi and one unit for each output class qj, the Bayes theorem provides the equation, shown in FIG. 1B, for the probability of $q_j$ conditioned on x.

With further reference to FIG. 1B, ordinarily, the computation involves taking the logarithm, in which case the right-hand side becomes a discrete sum. Each term corresponds to the coefficient (weight) associated with input variable $x_i$ to the output class $q_j$. Each output class unit sums its inputs and exponentiates the result, yielding the desired probability. In the network shown in FIG. 1A, there is one 'complex' or 'compound' column variable (ab) and one simple first-order column variable (c).

One of the goals of spontaneous reporting systems is to protect the public health by providing an early warning system for previously unknown serious adverse drug reactions (ADRs). A driving principle of these systems is the suspicion of possible causal relationships between AEs and drugs, which prompts the reporter to submit a spontaneous report. In the course of investigating these reports, drug safety personnel may receive information on events, adverse or otherwise, that occurred after the drug was administered, but were not the intended subject of the spontaneous report. These events which did not prompt contact with the pharmaceutical company or regulator and for which there is no evidence of drug causality are usually defined as 'incidental events' by the Council for International Organizations of Medical Sciences (CIOMS) V Working Group. However, the "absence of evidence" of causality does not constitute "evidence of absence" per se. It frequently happens that an evidence of a safety signal or a causal relationship simply has not been noticed or reported by humans Data analysis methods that have been used with spontaneous report data include the Multi-Item Gamma Poisson Shrinker (MGPS), the Proportional Reporting Ratio (PRR) method, and the Bayesian Confidence Propagation Neural Network (BCPNN). However, none of these methods has previously been supported with a system and method that (1) automatically insures that the exposed and non-exposed groups have comparable attributes and clinical needs that must be addressed therapeutically with some drug or intervention or combination of drugs or interventions, nor are the prior art methods capable of (2) adaptively and automatically examining interactions beyond first-order "drug-event" pairs.

Embodiments of the invention are directed to reliably detecting diagnostic-yield signals and/or safety signals that include not only first-order but also second- and higher-order combinations and sequences of markers or therapeutics that are associated with diagnostic outcomes or adverse events/undesirable outcomes. Some embodiments utilize BCPNN, MGPS, and PRR to multi-laterally ascertain statistically significant increases or decreases in the relative risk of specific outcomes that are associated with various phenotypic markers or therapeutic interventions (such as specific medications or combinations of medications or specific doses or cumulative exposures to a medication or combination; or invasive procedures such as surgeries; or plans of care or treatment protocols) in the context of the population attributes and severity of illness attributes that are of interest. Some embodiments match sub-cohorts based on attribute vectors of diagnoses and correlate these with the approved clinical on-label indications for various medications. This matching forms the basis for assembling appropriate aggregates of exposed and non-exposed subjects, so that false-positive and false-negative error rates of signal detection are substantially reduced compared to prior art systems. Control of false-positive error is performed using an FDR algorithm, such as that of Benjamini and Hochberg, in a manner similar to FDR usage in genomic microarray data analysis.

Some embodiments of the invention address the problem of cost-effective genomics testing and WGS/WES diagnostic-yield signal detection in a genomics-oriented diagnostic testing service. Methods that are conventionally used for the evaluation of diagnostic-yield signals are inconsistent and sometimes of poor quality, as described herein.

Some embodiments of the invention address the problem of safety signal detection and validation and tracking, primarily as part of an observational program of vigilance following regulatory approval of a therapeutic health product, such as a drug or a biologic or a medical device, or of an interventional procedure or service. Other methods that are conventionally used for the evaluation of drug safety signals (including major signals leading to withdrawal of products from the market) are inconsistent and sometimes of poor quality. While the assessment of the safety of medicines and other therapeutics needs to consider specific issues such as drug interactions and variation in compliance, the general principles, which are used to study environmental hazards, can be applied for this purpose. The criteria proposed more than 35 years ago by Austin Bradford-Hill for attributing disease or health outcome causation to environmental factors have been used widely in epidemiology, are today widely applied to pharmacovigilance and pharmacoepidemiology. The Austin Bradford-Hill criteria include strength and consistency of evidence; statistical specificity; temporality of the adverse event to exposure to its putative cause(s); biological gradient associated with increased incidence of the adverse event; causal plausibility; and logical and mechanistic coherence.

But these other methods and conventional methods used for the evaluation of diagnostic-yield signals have several limitations, including:

(1) To detect a diagnostic-yield signal or safety signal, human beings, who have finite attention spans and finite scope of responsibility and authority with regard to performing surveillance and comprehending the various attributes or exposures and outcomes that arise for any one patient or for a population of patients in their care, must perceive patterns of multiple antecedent variables and multiple events and outcomes that may potentially be caused by or consequent upon these patterns, thereby constituting an unexpected occurrence relating to diagnostic-yield or safety. Upon noticing such a pattern occurrence, they must further take the initiative to electively document the event and pattern and manually record it in the medical record. This contributes to substantial under-reporting of findings and patterns that are subtle or materialize over a long span of months or years. With regards to safety signals, they must manually submit a spontaneous adverse drug report (ADR) or an adverse event report to the relevant regulatory or public health agency. The fact that these acts take time, for which the submitters receive no compensation, leads to significant under-reporting and a dearth of submissions. Furthermore, the fact that, in many cases, the humans perceive substantial medical malpractice or other risk that would be incurred were they to undertake to report an event or pattern that they have witnessed contributes to substantial under-reporting of adverse events.

(2) Frequently, humans fail to notice relevant patterns. Often, this is because the patterns involve multiple variables that collectively constitute the pattern or criteria that define the diagnostic status or event. Sometimes it is because the multiple variables include some that are beyond the scope of any particular individual's responsibility to observe or understand. The person who orders one test or panel of tests may not be responsible for monitoring the results of tests that are ordered by other persons or that are ordered at different times in the course of care. As a result of this fragmentation of responsibility and oversight, diagnostic-yield signals or safety signals that involve multi-variable patterns are distinctly unlikely to be detected or spontaneously reported by anyone involved in the care process.

(3) With regards to safety signal detection, the psychology of physicians and other providers who care for patients facing serious and life-threatening conditions is such that they are less likely to spontaneously report adverse events involving therapeutics that were prescribed in an attempt to save the patients' lives. In such contexts, the nature of the therapeutic doctor-patient relationship is such as to be biased against spontaneous reporting, insofar as the mortality and other risks that are inherent in the context are already large and clinicians have difficulty ascertaining whether a serious adverse event that does occur is 'incidental', or would have occurred anyway, or whether by contrast it is an event that may be causally related to the therapy chosen and constitutes an unreasonable balance of marginal risks that are not outweighed by major benefits of the therapeutic choice. It is far easier to discern rare and unexpected serious adverse events and causal relationships among relatively "well" ambulatory patients. As a result, there are significant under-recognition and under-reporting of adverse events and product safety issues in acute-care hospital populations, in long-term care and nursing home populations, and in other populations that have relatively high morbidity and severity-of-illness.

(4) Some important abnormalities or patterns of findings arise with such low frequency that, although serious, it is improbable that any one practitioner would encounter even one of them during their practice lifetime. Similarly, some important adverse reactions or safety event types arise with such low frequency that, although serious or life-threatening, it is improbable that any one practitioner would encounter even one of them during a lifetime of practice. As such, even the practitioner who does encounter one or two occurrences is often disposed to regard the events as 'incidental' or random. In the absence of strong financial or other incentives to think deeply about the occurrence and attempt to understand it or report it, the natural tendency is to dismiss it without reporting it and proceed on to the care of other patients.

(5) With regards to safety signal detection, episode-oriented case-level and longitudinal patient-level information are neglected, often omitted from regulatory agencies' spontaneous reporting forms. Instead, only event-level information is captured. This 'collocation', event-scoped regime inadvertently and powerfully disincentivizes the recognition of concomitant and longitudinal exposures that transgress the boundaries of the index episode in which the current event or case arises, with consequent false-negative errors (failure do detect true safety signals).

(6) With regards to safety signal detection, some data mining techniques utilize processing methods that result in substantial delays in signal detection, compared to conventional spontaneous adverse report safety analyses.

(7) With regards to safety signal detection, what is happening in practice is that drug manufacturers must report AEs and ADRs in such a way that they are indistinguishable from each other in the spontaneous reporting databases. In addition, seriousness is recorded on reporting forms and electronic file formats at the "case" level and not at the "event" level. This results in an inability to discriminate serious from nonserious adverse events. Both of these issues result in excessive false-negative (Type II) involving serious adverse events and false-positive (Type I) errors involving nonserious and/or incidental adverse events, which impairs the ability of reviewers to detect true serious safety signals and protect the public health.

(8) Some data mining techniques depend either on (a) absolute uniformity in nomenclature, which tends to limit the size and diversity of systems that are able to contribute to the data warehouse for data mining and signal detection, or they depend on (b) loose textual or semantic matching, which is valuable for some case-finding (positives) but often is unable to accurately ascertain exposures and nonexposures and is likewise often unable to accurately rule-out or ascertain nonoccurrences (negatives). Consequently, automatic inter-systems ontology mapping services are important in order to achieve repositories having adequate sample size and diversity such that interpretations are not statistically confounded by unmeasured factors that are associated with the use of any particular vendor's EMR or other source system recording the attributes or exposures and outcomes or events that materialize subsequent to the care episodes or exposures.

(9) Alternative prior art solutions that require detailed construction of database retrieval extracts where the extracted cohorts embody homogeneous populations give rise to labor-intensive activities requiring individuals of high levels of expertise. As a result, such systems are too expensive to operate on a comprehensive or sustainable basis.

(10) Prior art methods are not able to accommodate the very large proliferation of markers or outcome-types or event-types that would occur if features or events were stratified according to their severity or according to their duration or reversibility. But if there is a physiologic mechanism whereby a disease causes a marker or an agent causes an outcome, one naturally expects to find a quantitative dose-response relationship in the data, where increasing quantitative exposures or copy number variation (CNV) are associated with more frequent, severe, or persistent features or marker values or are associated with more frequent, severe, longer-lasting, or irreversible outcomes. The binomial analysis limitation of prior art methods results in significant false-negative errors. An important capability to detect causal relationships from quantal strata is foregone.

(11) With regards to safety signal detection, prior art systems are in general unable to discern differences among different strengths or mg/kg dosages or particular dosage-forms or routes of administration or, for medical devices, are unable to discern differences among various versions or models or sizes or peri-procedural constellations of collateral treatments or other factors. Instead, they are only able to do case-finding and analysis upon coarse, binomial "exposed"/ "not-exposed" status.

(12) While some EMR-based methods have recently appeared, these do not properly balance the comparator population against the attributes of the candidate population for adverse event discovery and ascertainment.

(13) Prior art solutions that are based on administrative transactions, prescriptions, orders, claims, and other episode-scoped information often lack detailed date-time stamped information denoting the minute-wise timing of when medication-administration exposures occurred and when any events materialized. As such, all such systems are able to ascertain is simple statistical 'association', not causality. By contrast, some modern EMR systems capture such detailed exposure and laboratory test result and clinical event information for each item with minute-wise precision. Additionally, some such EMR systems record the excursions that frequently happen when physicians modify patients' orders over time—involving exposure (therapeutic "challenge") for a period of time; dose-range adjustment of the dose or concomitant medications over a subsequent period of time; discontinuation of therapy ("de-challenge") in yet a subsequent period of time, for one reason or another; and re-prescribing of the drug again over a period of time ("re-challenge"). These EMR systems capture these time stamped exposure excursions together with the date-time stamped succession of event occurrences such as materialize during these excursions. From such challenge-dechallenge-rechallenge excursions it is possible to deduce causal relationships. However, prior art systems fail to take advantage of this naturally-occurring data in modern EMR systems or data warehouse repositories derived from them.

(14) Conventional prior art methods emitting safety signals often leads to regulatory removal of the product from the market, when in fact no safer effective alternative exists. In other words, such systems are logically similar to "placebo-controlled" clinical trials that imply that "not treating" the condition is a viable, rational, ethical option, which is not true. It is neither rational nor ethical in a majority of instances. Therefore, instead the comparator group for safety signal detection should preferably be restricted to individuals who are receiving some sort of treatment ("active control") for the condition of interest.

Accordingly, it is therefore valuable and desirable to provide embodiments of the methods and systems described herein for ameliorating these limitations. The current state of knowledge about sentinel combinations of phenotypic markers or unsafe combinations of therapeutic interventions is limited by the finite ability of human beings to notice and understand complex multivariable patterns of information, especially causative patterns or chains of events that unfold over a period of time or ones that transcend the customary scope of responsibility and authority that a particular person has. Consequently, diagnostic issues with such multivariable patterns either remain undetected, or else expensive WGS or WES are undertaken but only yield a positive diagnosis in only 20% to 40% of the persons tested.

Pairwise drug-drug interaction databases reflect the ability of humans to notice and report adverse outcomes that arise when two things in combination are associated with one event type that is proximate in time to the exposure to that combination. However, patterns of interactions that involve three or more drugs or combinations of one or more drugs concomitantly with multiple patient attributes or one or more antecedent therapeutic procedures are well beyond the abilities of average humans to notice or comprehend. Consequently, safety issues with such multivariable patterns presently remain undetected, and guidances warning against them are never published.

Accordingly, embodiments of the invention provide systems and methods for detecting such characteristic patterns and diagnostic-yield signals or safety signals; establishing them in defined, context-specific populations where their meaning and statistical significance can be reliably interpreted; and tracking the incidence and evolving statistical strength of the diagnostic-yield signals or safety signals over time.

Moreover, with regards to detecting diagnostic-yield signals, mining frequent itemsets is a popular method for finding associated items in databases. For this method, support, the co-occurrence frequency of the items which form an association, is used as the primary indicator of the associations' significance. A single user-specified support threshold is used to decide if associations should be further investigated. Support has some known problems with rare items, favors shorter itemsets and sometimes produces misleading associations.

The main advantages of using support are that it is simple to calculate, no assumptions about the structure of mined data are required, and support possesses the a so-called downward closure property which makes a more efficient search for all frequent itemsets in a database possible. However, support has also some important shortcomings, including (1) it discards itemsets with low support and (2) it disproportionately favors smaller itemsets while longer itemsets could nonetheless have value, even if they occur less frequently.

Heterogeneity in the occurrence frequencies between items is accounted for by the form of the mixing distribution. A commonly used and very flexible mixing distribution is the Gamma distribution or Negative Binomial distribution. The Negative Binomial distribution is widely and successfully applied for actuarial statistics, birth-and-death processes, and economics. In some embodiments of the invention, a Negative Binomial association rule-mining method is utilized to produce a marker frequent itemset that is suitable for subsequent analysis by BCPNN, MGPS, and related signal-detection methods for determining high-utility marker sets that are likely to achieve high diagnostic yield in WGS or WES testing.

Figure 2A:
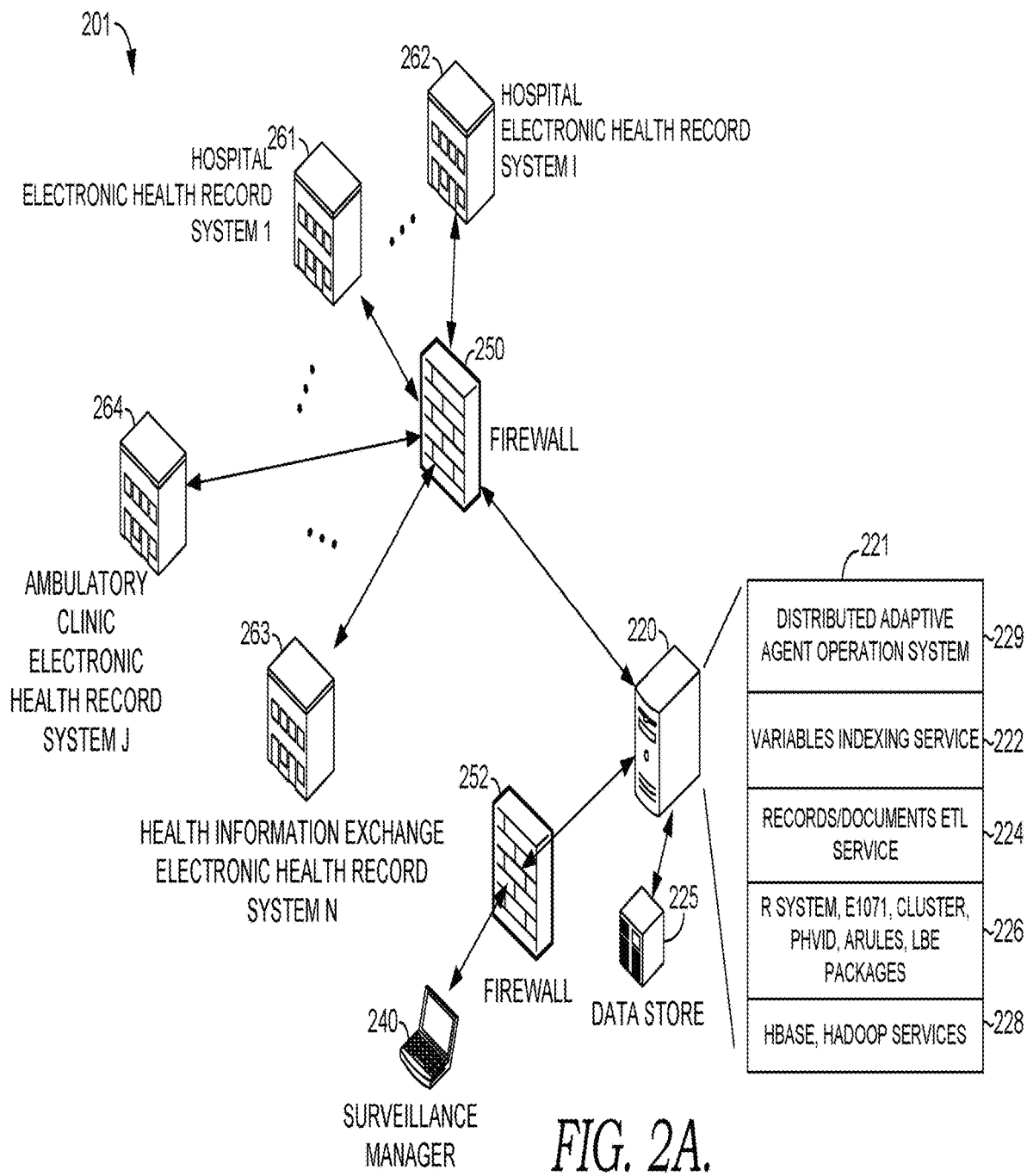
FIGS. 2A, 2B, and 2C depict aspects of an illustrative operating environment suitable for practicing embodiments of the invention.
Figure 2B:
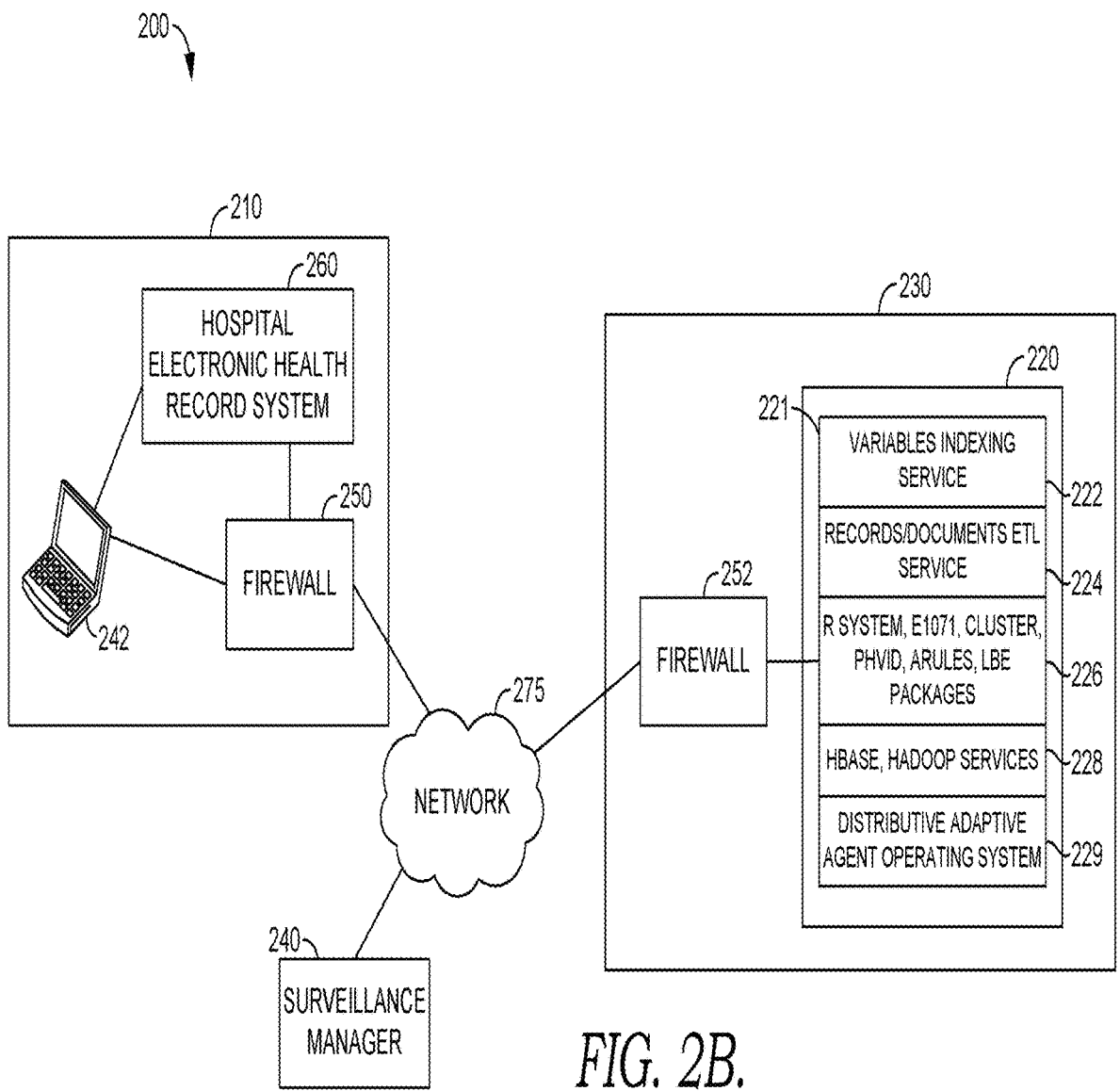

Turning now to FIG. 2A and 2B, there is presented example operating environments suitable for practicing embodiments of a marker screener system and event surveillance system ("screener system"). With reference to FIG. 2A, example operating environment 201 includes a computerized system for compiling and running an embodiment of the screener system. In this example operating environment, one or more health record systems such as, for example, Hospital Electronic Health Record System 261, Hospital Electronic Health Record System 262, Ambulatory Clinic Electronic Health Record System 264, and Health Information Exchange Electronic Health Record System 263, are communicatively coupled to a network behind firewall 250, which is communicatively coupled to computer system 220. In embodiments, components of 201 are communicatively coupled over a local or distributed network (not shown) such as the Internet, a public network, or a private network. Embodiments of electronic health record (EHR) systems 261, 262, 263, and 264 include one or more data stores of health records and may further include one or more computers or servers that facilitate the storing and retrieval of the health records. Firewall 250 may comprise a separate firewall associated with each EHR system, in some embodiments. Furthermore, in some embodiments, one or more EHR systems may be located in the cloud or may be stored in data stores that are distributed across multiple physical locations. In some embodiments, examples of EHR systems further include record systems which store real-time or near real-time patient information, such as wearable, bedside, or in-home patient monitors, for example.

Continuing example operating environment 201 further includes computer system 220, which may take the form of a server, which is communicatively coupled through firewall 250 to EHR systems 261, 262, 263 and 264, and also through firewall 252 to surveillance manager 240. In embodiments, surveillance manager 240 may take the form of a software application operating on one or more mobile computing devices, tablets, smart-phones, front-end terminals in communication with back-end computing systems terminals, laptops or other computing devices. In some embodiments surveillance manager 240 includes a Web-based application or collection of applications that is usable to manage services provided by embodiments of the invention. For example, in an embodiment surveillance manager 240 includes one or more applications for managing diagnostic testing.

Embodiments of computer system 220 include computer software stack 221, which in some embodiments can operate in the cloud, as a distributed system on a virtualization layer within computer system 220. Some embodiments of software stack 221 include a distributed adaptive agent operating system 229, which is capable of hosting a number of services such as 222, 224, 226, and 228. Embodiments of services 222, 224, 226 and 228 can run as a local or distributed stack on a collection of personal computers and servers such as 220 and/or a computing device running manager 240. In one embodiment, manager 240 operates in conjunction with software stack 221.

In embodiments, variables indexing service 222 and Records/Documents ETL service 224 provide services that facilitate retrieving frequent item sets, extracting database records, and cleaning the values of variables in records. These services may invoke software services 226, which may be embodied as one or more software agents, applications or routines such as the example embodiments of computer program routines illustratively provided in FIG. 6. Software services 226 perform statistical software operations, and may utilize statistical calculation packages such as, in one embodiment, the R system (i.e., the R-project for Statistical Computing, which supports packages or modules of software functions tailored for specific statistical operations, sometimes called R-packages, and which is accessible through the Comprehensive R Archive Network (CRAN) at http://cran.r-project.org); R-system modules or packages may include rms (regression modeling strategies), e1701, arules (titled Mining Association Rules and Frequent Itemsets) or arulesNBMIner software package (titled Mining NB-Frequent Itemsets and NB-Precise Rules), cluster, PhViD, which is an R package for Pharmaco Vigilance signal Detection that includes functions for computing Bayesian Conditional Probability Neural Network (BCPNN) values, and the BioConductor module LBE. Module LBE provides a procedure for false-discovery rate (FDR) control, or more specifically, for estimating the proportion of true null hypotheses, the false discovery rate (and so the q-values) in the framework of estimating procedures based on the marginal distribution of the p-values without assumption for the alternative hypothesis. Software packages 226 are associated with services 228, which include Apache Hadoop and Hbase framework, or similar frameworks operable for providing a distributed file system.

Example operating environment 201 also includes data store 225, which in some embodiments includes patient data and information for multiple patients; variables associated with patient recommendations; recommendation knowledge base; recommendation rules; recommendations; recommendation update statistics; an operational data store, which stores events; frequent itemsets (such as "X often happens with Y," for example) and itemsets index information; association rulebases, agent libraries, and other information, patient-derived data, health care provider information, for example. Although depicted as a single data store, data store 225 may comprise one or more data stores, or may be in the cloud.

FIG. 2B illustratively depicts another aspect of an example operating environment, referred to herein as 200. Within 200, a first premise location 210 includes a network behind firewall 250 communicatively coupled to network 275. In some embodiments, network 275 includes the Internet, a public network, or a private network. Premise location 210, which may comprise multiple separate geographical locations, further includes EHR system 260, which may comprise multiple separate EHR systems communicatively coupled through a network, as depicted in FIG. 2A. In some embodiments, premise location 210 further includes client computer 242, which communicates with EHR system 260. Example environment 200 further includes a premise location 230 which includes computer system 220 communicatively coupled through firewall 252 to network 275. Additional numbered components of environment 200 in FIG. 2B are described in connection to FIG. 2A.

Figure 2C:
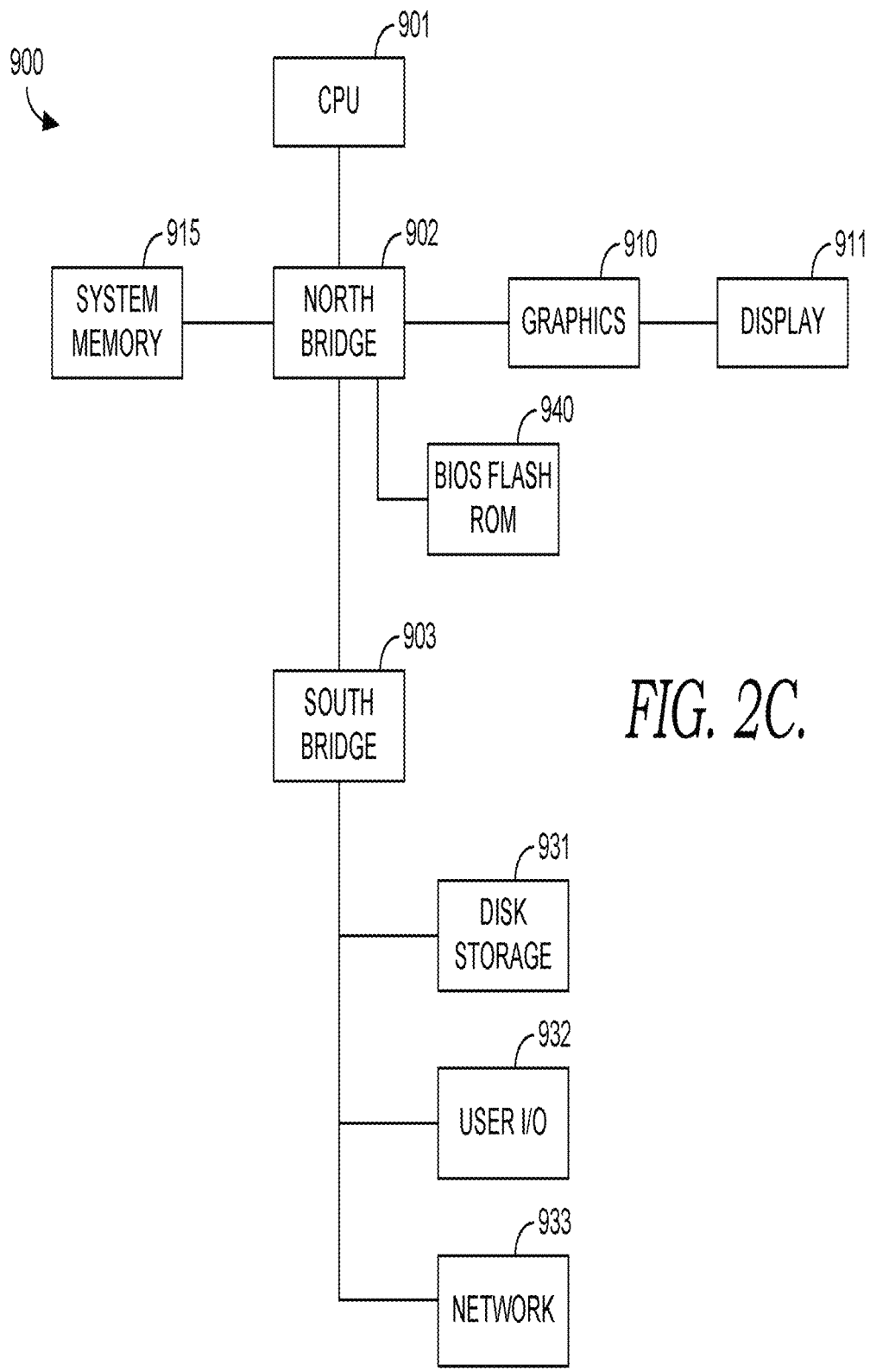

Turning now to FIG. 2C, there is shown one example of an embodiment of computer system 900 that has software instructions for storage of data and programs in computer-readable media. Computer system 900 is representative of a system architecture that is suitable for computer systems such as computer system 220 of FIGS. 2A and 2B, and the computer device(s) operating surveillance manager 240, in some embodiments. One or more CPUs such as 901, have internal memory for storage and couple to the north bridge device 902, allowing CPU 901 to store instructions and data elements in system memory 915, or memory associated with graphics card 910 which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU through south bridge 903 as well. The system architecture depicted in FIG. 2C is merely one example of any number of computer architectures suitable for supporting computer system 220 of FIG. 2A and 2B.

In some embodiments, computing system 900 is a computing system made up of one or more computing devices. In an embodiment, computing system 900 includes an adaptive multi-agent operating system, but it will be appreciated that computing system 900 may also take the form of an adaptive single agent system or a non-agent system. Computing system 900 may be a distributed computing system, a data processing system, a centralized computing system, a single computer such as a desktop or laptop computer or a networked computing system.

In some embodiments, computing system 900 is a multi-agent computer system with software agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 3A:
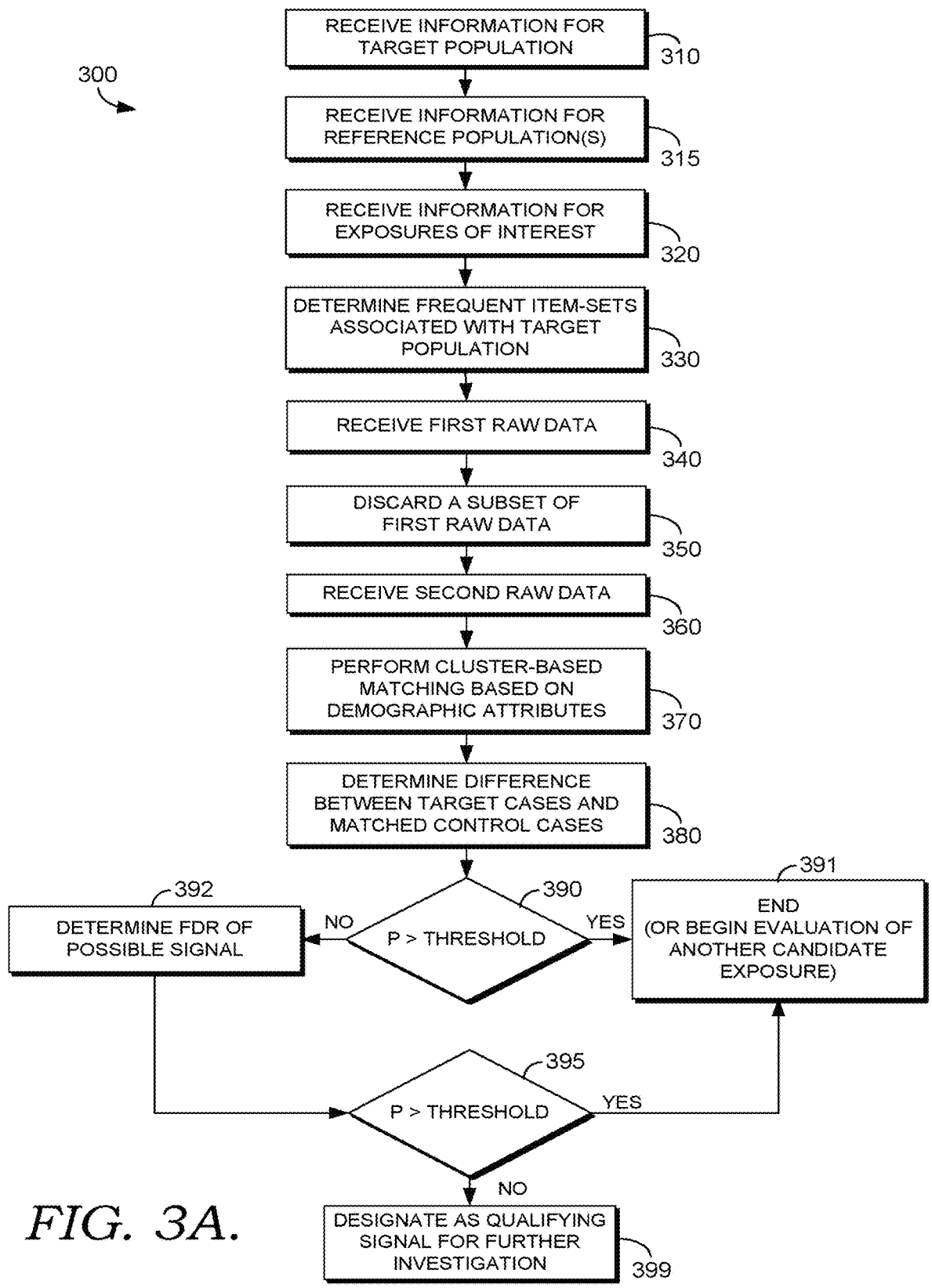
FIG. 3A depicts a flow diagram of a method for generating a synonymy classifier and verifying and validating whether such a classifier achieves statistical sensitivity and specificity in the range of deployment, sufficient for satisfactory performance in the use for detecting and ascertaining safety signals or diagnostic-yield signals in observational data warehouses comprised of records derived from electronic medical records (EMR) systems, in accordance with embodiments of the invention.

Referring to FIG. 3A, a flow diagram is provided which illustrates an embodiment of a method for generating a synonymy classifier and verifying and validating whether such a classifier achieves statistical sensitivity and specificity in the range of deployment, sufficient for satisfactory performance in the use for detecting and ascertaining diagnostic-yield signals or safety signals in observational data warehouses comprised of records derived from electronic medical records (EMR) systems, herein referred to generally as method 300. In some embodiments, method 300 utilizes the computer program routine illustratively provided in FIG. 6.

At a step 310, a first set of health care information about a target population of interest is identified and received. At a step 315, a second set of health care information about a reference population of interest is identified and received. In some embodiments a computer system 220 receives the sets of information from one or more EHR systems such as 260, 261, 262, 263, and/or 264, or from network storage such as data store 225, which may comprise one or more EHR systems, in some embodiments. In some embodiments a user or software agent selects the target and reference populations of interest by establishing attributes and/or inclusion-exclusion criteria and venues that define that population.

At step 320 the exposures of interest, including diagnostics exposures or therapeutics exposures that are incident upon members of the population, are identified and received. In some embodiments, exposures of interest include a drug, ingested food, or liquid; product; an environment or an event incident upon a patient, or combination of these. For example, in a target patient population comprising 35- to 60-year-old heart attack patients having an in-patient length of stay greater than 72 hours, an exposure of interest might comprise those patients who were prescribed Ciprofloxacin. In some embodiments, exposures of interest are selected by a user or software agents or recommended by computer system 220. In some embodiments, exposures of interest are received from a recommendation provided by a software agent and/or computer system 220; from software-logic rules such as, for example, the top 500 drugs prescribed most often over a period of time; or inputted by way of a user selection or query.

At a step 330, frequent item-sets associated with the population are determined. In some embodiments, method 300 retrieves frequent item-sets that are statistically associated with the population, including exposures and outcomes events (such as procedures, or statuses, or laboratory results, or clinical exam findings, or diagnoses, for example), with provision for longitudinal record linkage for markers or diagnoses or for outcomes that tend to materialize after a latency period has elapsed. In some embodiments, step 330 includes step 320, and in some embodiments, computer system 220 and/or software agents identify exposures of interest by determining frequent item-sets associated with the target population.

In some embodiments, EHR systems or data store 225 are queried for information used to identify frequent item-sets. In some embodiments, one or more software agents, operating as part of a multi-agent computer system 220, facilitate identifying and retrieving frequent item-sets, and in some embodiments, the arules or arulesNBMIner open-source software packages of the R-system (or R-project), which is depicted as part of services 226 of FIGS. 2A and 2B, is employed. In some embodiments, a solver agent applies the arules or arulesNBMIner package, and in some embodiments a plurality of software agents may be used, operating in parallel, for determining frequent item-sets from the set of information.

At a step 340, a portion of raw data of the target population identified in step 310, herein referred to as the first raw data, is received. In some embodiments for detecting safety signals, the first raw data is selected or extracted from the information about the target population, and comprises samples of EHR database records that accrued during a surveillance time period. In embodiments, a first portion of raw data is identified and received from the target population for processing by the present method. Embodiments select the exposures of interest identified at 320 in addition to ancillary demographic data associated with identified data items for each instance of care. Examples of demographic data may include the patient type, reason for admission, patient height, patient weight, patient age, patient race, patient sex, units, item description, item notes, reason for care, venue type: home, clinic, emergency, outpatient, surgery, or similar data associated with the patient. In some embodiments data is selected by forming an SQL query over available records identifying necessary data, and restricting records that are within certain ranges of demographic data so as to make the selected data homogeneous. Some embodiments restrict the sex, weight, patient age, or care context so as to restrict the chosen records to a certain, chosen, homogeneous demographic subset.

At a step 350, a subset of the first raw data is discarded. In some embodiments, marker-diagnoses combinations or exposure-event combinations that do not have any occurrences or have fewer than a "Q" counts during the period being analyzed or a period of surveillance are censored. Moreover, in some embodiments the value of Q counts varies according to the marker-diagnoses or event-exposure combination. For example, in the embodiments described in connection to FIGS. 4A and B and FIG. 5, event exposure combinations having fewer than three occurrences (Q=3) during a period being analyzed are removed from the raw data. However, the value of Q may vary to accommodate different sensitivities, rationalized by different use-cases, occurrence ascertainment methods, and value gained/lost by occurrences. Specifically, increasing the Q value would tend to reduce the statistical sensitivity to detect true-positive signals, in principle. The minimum count Q that may be considered actionable may vary according to the event-type, according to the reliability of the method(s) used to ascertain the occurrence or non-occurrence of that event-type, and according to the value associated with the occurrence of the diagnostic-yield or safety event (for example, a reversible event; irreversible event; death of a child who was otherwise well; death of a healthy adult with many dependents; death of an elderly person; death of someone so sick that their survival was improbable no matter what therapeutic regimen might be tried; or similar events).

At a step 360, a portion of raw data of the one or more reference populations identified in step 315, herein referred to as the second raw data, may be received. Some embodiments of step 360 identify records from the one or more reference populations that meet the same demographic restrictions that were applied in the selection of the raw data at 340. For example, if the target population is heart attack patients having an in-patient stay of greater than 72 hours, with demographic attributes that identify males, ages 35 to 70, then a subset of information, which comprises the second raw data, is selected or extracted from the one or more reference populations to be restricted to similar demographic attributes, in order to provide a better statistical sample for comparison.

In some embodiments, the data records' variables values received at step 340 and 360 are first "cleaned" or otherwise prepared for processing by services 222 and 224 of FIGS. 2A and 2B. For example, some embodiments clean the data for uniformity, and some embodiments transform data values to a new interval for comparison, and discard data that does not meet quality standards. For example, if a numerical field has a textual entry, this data is discarded, or converted to a numerical value, or if data is in various units, the data is converted to standard units for comparison purposes. Additional examples of discarding data include discarding extreme values from raw data, e.g. default values or obviously erroneous values.

At a step 370, perform cluster-based matching of the reference instances (i.e., information from the reference populations comprising patients who did not receive the WES or WGS testing and have particular marker sets or patients who did not have the candidate exposure-event of interest, which serves as a control), to target instances (i.e. information from the target population who did receive the WES or WGS testing and have particular marker sets or who receive the candidate exposure). In embodiments, the cluster-based matching is based on the demographic attributes, and is applied to the first raw data from the subset of second raw data to determine one or more clusters. Embodiments apply a cluster method to reduce the dimensionality of the raw data. Some embodiments of applying a cluster method generate a decision-tree classifier. For example, a representative clustering method identifies a first cluster of numeric data and a second cluster of alphabetic data. Another representative clustering method breaks down the data values of a field to be analyzed into a spectrum of numerical values and identifies clumps of values that are relatively close to one another. An exemplary clustering method identifies clusters based on demographic attributes, e.g. breaking down by gender, race, units, description content, notes content, etc.

In some embodiments, the open-source module e1017, a software package in the R-system of services 226 in FIGS. 2A and 2B, is employed to facilitate one-to-one matching against the demographic attributes. For example, for everyone who is a woman, age 37, African-American, has comorbid diabetes with a heart attack, find another patient from the unexposed (reference) population in the cohort that also has these attributes. In embodiments e1071, or similar software services, have the functionality to account for slight variations in the matching attributes, and such variation can be adjusted by the user, in some embodiments. For example, a 36-year-old (instead of 37 year old) woman having the same attributes above may be determined as a match. In some embodiments, one or more software agents facilitate the matching processing, and operate in parallel, thereby allowing a large amount of information to be evaluated for matching in a reduced amount of time.

At a step 380, one or more quantitative measures of the degree to which the groups' diagnostic-yield rates or event rates differ between the first data of the target population and the second data of the reference group(s), for the target 'cases' and the matched 'controls' as determined in step 370.

In embodiments, measures of statistical difference are determined by employing the BCPNN algorithm and may be carried out using a software service 226 such as the open-source PhVid package, version 1.0.3 of the R-system. In some embodiments, the BCPNN algorithm is carried out in parallel with one or more of the MGPS, Emperical Bayes (EB) algorithm, and proportional reporting ratio (PRR) algorithms so that results of each of these algorithms may be provided to a user or software agent enabling the user or software routine (such as the example computer program routine provided in FIG. 6.) to compare the results for sensitivity in detecting the diagnostic-yield signals or safety signals.

At a step 390, the output measure P determined in step 380 is compared against a first threshold value to determine whether a statistically significant diagnostic-yield signal or safety signal exists for the candidate exposure of interest. For example, in embodiments, a comparison is performed, such as PRR >2; BCPNN probability <0.05; or MGPS probability <0.05, wherein a threshold value (e.g., 2 for PRR and 0.05 for BCPNN and MGPS) is empirically established as denoting statistically significant diagnostic-yield signals or safety signals. In some embodiments, a software agent determines the threshold value and may update or vary the threshold and additional information about patient populations and exposures becomes available. In other words, if the probability P is greater than the threshold, we can accept the null hypothesis that this drug (or other candidate exposure) is no different from all other drugs or exposures, and we can proceed to a step 391, where we quit or go on to next exposure candidate. However, where the probability P is less than the threshold, then there is possible signal(s) indicating that exposure to the candidate is likely to help or harm the patient's condition, or on the other hand, there could be excessive false alarms affecting the possible signal.

Accordingly, where P is less than the threshold, it is necessary in some embodiments, to assure that the signal(s) detected in step 390 are sufficiently unlikely to be false positives or false alarms. Thus, at a step 392 a false discovery rate (FDR) is determined. In some embodiments, an FDR is determined using the Benjamini-Hochberg or other methods for computing FDR. In embodiments, FDR sets a threshold for discriminating signals thereby controlling excessive rates of false alarms. By determining whether a signal is a false positive, a drug (or exposure) that would otherwise be removed from the market due to apparent danger, might otherwise remain. One practical consequence is that where such a drug is the only drug available on the market for a treatment, the drug remains on the market and patients may live instead of die.

At a step 395, the FDR-applied signal is compared against a second threshold value. Where the signal is greater than the threshold, there is likely a high number of false alarms, and the method proceeds to step 391. However, if the signal is lower than the second threshold, then the signal at step 399 is designated as a qualifying signal, potentially indicating that the candidate exposure has a bearing on the patient's disposition. In some embodiments, an ideal signal P maybe equal to 0.01 or less.

Figure 3B:
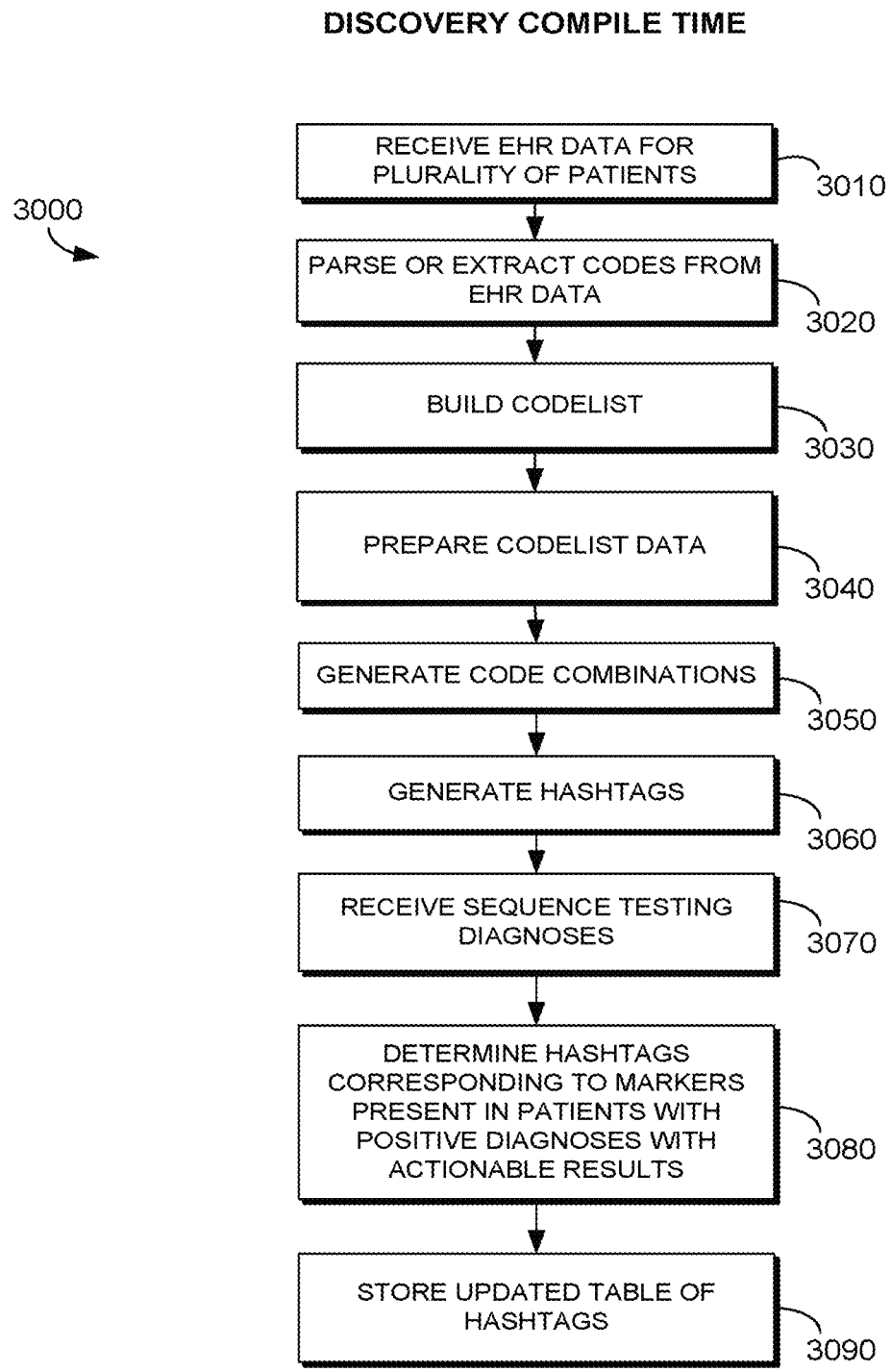
FIG. 3B depicts a flow diagram of an example method for determining a combination of one or more markers (or features) that are statistically significant for predicting the likelihood of getting an actionable diagnoses from WGS/WES sequence testing.

Referring to FIG. 3B, a flow diagram is provided which illustrates an embodiment of a method 3000 for determining a combination of one or more markers (or features) that are statistically significant for predicting the likelihood of getting an actionable diagnoses from WGS/WES sequence testing. At a step 3010, EHR data is received for a plurality of patients. Exposures may include phenotypic information in EHR data, which may be coded in nomenclature taxonomy, such as findings or phenotypic findings or "markers" having corresponding codes in SNOMED, HBO, etc. In some embodiments, the EHR data received comprises assessments and/or problem lists for the plurality of patients that include phenotypic information.

In some embodiments, the EHR data may be in a natural language format, such as physician notes, and may need to be parsed or analyzed for clinical codes using natural language processing, such as Cerner's nCode.® Accordingly, at step 3020, clinical codes are parsed or extracted from the EHR data. For example, the EHR data may comprise written notes about the patients, such as for a particular patient, the child looks differently, their developmental milestones (cognitive and motor milestones) are delayed, they are of short stature, in the $95^{th}$ percentile of body mass, etc. It is not uncommon for an assessment for a particular patient to be several pages in length. In some cases, for the problem lists, the phenotypic information may already be coded; thus step 3015 may extract these codes from a problem list table. Here, each code thus corresponds to a phenotypic finding—a feature or marker.

At step 3030, build a codelist based on the extracted phenotypic data. In an embodiment, the codelist comprises an array or table of the codes (parsed or extracted in step 3020) for each of one or more patients in the plurality of patients. At step 3040, prepare the codelist data. In some embodiments, preparing the codelist data includes deduplicating codes in the codelist, sorting the codelist, and/or promoting some codes to a super class. In particular, multiple repeating codes in the codelist can be removed (deduplication) and the codelist then sorted. In some embodiments, because of the number of codes present in some clinical coding nomenclatures, codes may be promoted to a super class or alternative code representing a broader category which includes more specific codes. The super class code is a coarser representation. (For example codes determined by a medical geneticist may be very precise/specific but codes determined by a general pediatrician may be more general. Thus in some embodiments, the more specific codes are recoded to be more general.

At step 3050, generate codes combination sets. In embodiments of step 3050, sets of code combinations are generated, wherein the set size comprises a number M of markers. In an embodiment, M is 5; thus step 3050 comprises generating combinations of up to 5 markers (represented as codes) from codes at a time in the codelist, such as C1 . . . C5 combinations. Typical syndromes or phenotypic findings have about 5 features or markers present in the patient. (The statistical likelihood of a patient having more than 5 markers is significantly small.) For example, the combination may include 5 markers taken one at a time, 5 markers present at once, two markers at a time, etc. (For example, for a combination of two, the combination may include a code corresponding to a patient having a flat face and a code for epicanthal folds in the eyelids. Thus patient having both of these things would correspond to this particular combination of codes. During the runtime portion of the method, described in FIG. 3C, some embodiments match combination code sets for a target patient with the combinations determined here.)

At step 3060, hashtags are generated for each combination of codes determined in step 3050. In an embodiment, the hashtags comprise a table of hash keys. For example, if the codelist includes 12 codes (12 markers or features) taken in combinations of up to 5, then approximately 1500 combinations will be determined in step 3050, and thus approximately 1500 hash keys will be generated. Each hash key may represent a possible combination of the markers, and thus patients with the same markers or features present) will have the same corresponding hash key. The hash keys provide efficiency and a unique identification for a particular combination, but are not necessary in all embodiments. Thus it is contemplated that some embodiments may not use hash keys but rather perform matches (as described herein) on the codes, code combinations, markers, or other data.

At step 3070 receive diagnoses of sequence test results. Embodiments of step 3070 may include receiving positive and negative sequence testing results for the plurality of patients. At step 3080, determine which hash keys (combinations of codes corresponding to combinations of markers) correspond to positive diagnoses that produced actionable results. In other words, for positive diagnoses with actionable results, determine the combination(s) of markers present in those patients. In embodiments, store or associate the diagnoses in the hash keys corresponding to the combinations of markers present in those patients.

In some embodiments, a new hashtag or hashkey is created in step 3080. In one embodiment, this hashtag may be represented in a format (or variation of) "M_xxx, DX_yyy, n11, sig_ind" where M_xxx represents a hash value for the particular combination of codes or markers (phenotypic findings). M may also represent the number of findings; DX_yyy corresponds to the particular diagnosis, such as a singular diagnoses from the sequence testing, which may be represented by a SNOMED code or other clinical nomenclature code; n11 represents the number of positive sequence diagnoses identified so far; and sig_ind represents a binary signal (e.g. 0 or 1) indicating the statistical significance of the relationship of the combination of markers to the likelihood of getting an actionable diagnoses from the WGS/WES testing, where in this particular embodiment 1 corresponds to a statistical significance. In some embodiments, a threshold with $p < 0.05$ may be used for determining statistical significance. Once method 3000 has gathered enough data to show significance, then sig_ind of 0 is changed to sig_ind=1. An example embodiment of a hash table using this example format is provided in FIG. 5C.

Turning briefly to FIG. 5C, a table is shown of hash keys. In some embodiments, the table shown in FIG. 5C may be used by the example computer program of FIG. 6 to produce signal indicators (sig_ind) values of "0" or "1." In the particular example embodiment shown in FIG. 5C, each hash key begins with a three-digit hash ID as the first number followed by the format M_xxx; DX_yyy; n11, described in the preceding paragraph.

Returning to FIG. 3B, the output of step 3080 may comprise a set of hash keys (also referred to as hashtags or hashes) such as depicted in FIG. 5C, which may be stored in step 3090. Method 3000 may continue to dun and update the data (e.g. the sig_ind) as new determinations are discovered. Additionally, in some embodiments the collection of hashes may be used in a runtime environment for identifying a target patient for whom the WGS/WES sequencing would likely produce an actionable result or a patient for whom such testing would not likely produce an actionable result. In particular, in some embodiments this may be carried out by matching combinations of markers corresponding to the target patient with the combinations determined in method 3000 using method 3100 described in FIG. 3C or method 300 described in FIG. 3A (e.g. by using the BCPNN, MGPS, or PRR statistical measures).

Figure 3C:
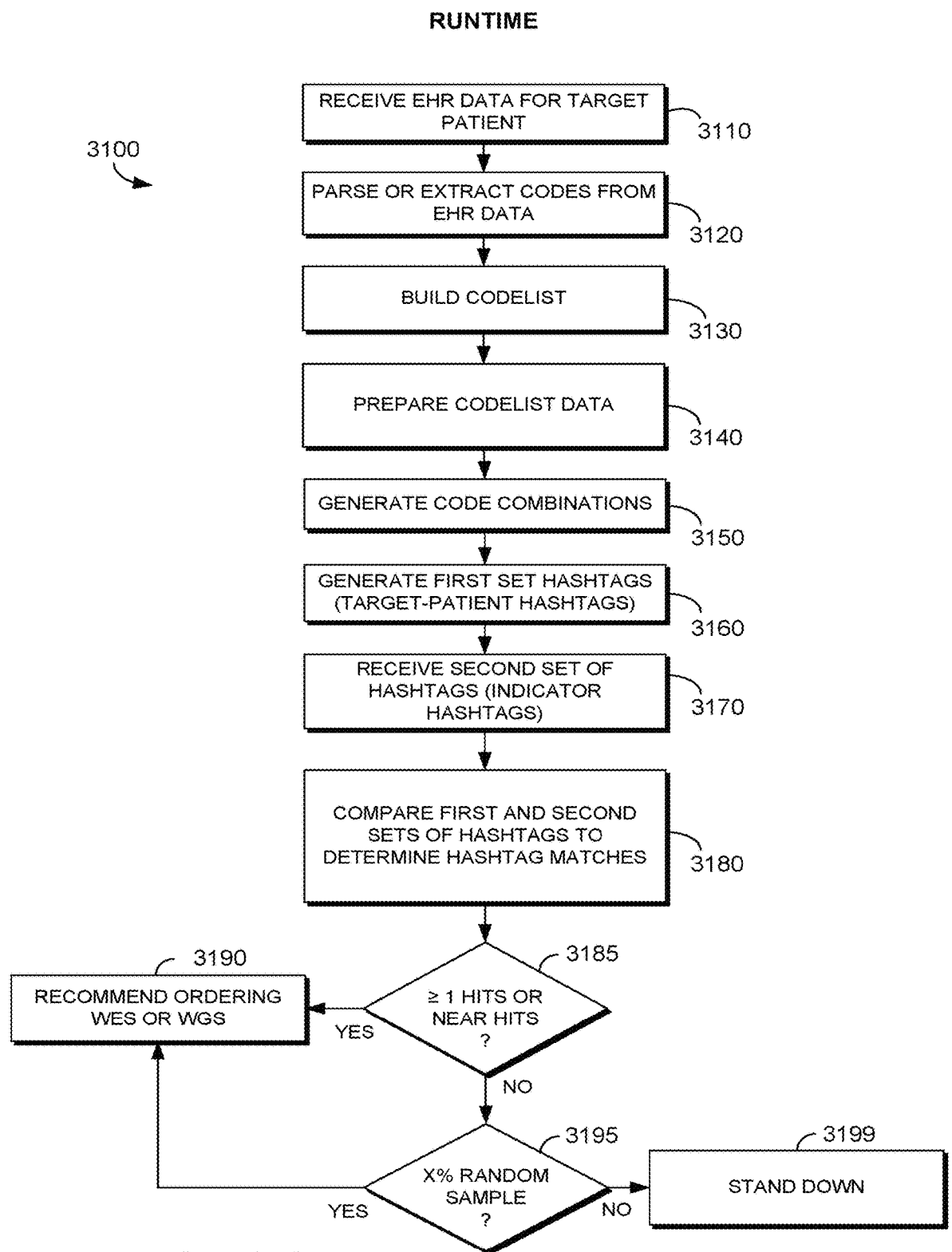
FIG. 3C depicts a flow diagram of an example method for identifying a target patient for whom the WGS/WES sequencing would likely produce an actionable result or a patient for whom such testing would not likely produce an actionable result.

Turning now to FIG. 3C, a flow diagram is provided which illustrates an embodiment of a method 3100 for identifying a target patient for whom the WGS/WES sequencing would likely produce an actionable result or a patient for whom such testing would not likely produce an actionable result. Method 3100 begins with steps 3110 through 3160, which may be carried out as described in connection to steps 3010 to 3060 in method 3000. Accordingly, at step 3110, EHR data is received for a target patient. At step 3120, clinical codes are parsed or extracted from the EHR data. At step 3130, build a codelist based on the extracted phenotypic data. At step 3140 prepare the code list. At step 3150, generate codes combination sets. At step 3160, a first set of hashtags are generated for each combination of codes determined in step 3150. The set of hashtags correspond to combinations of markers for the patient, and thus may be designated or referred to as the set of target-patient hashtags.

At step 3170, receive a second set of hashtags. The second set of hashtags may be all or a portion of the hashtags generated in method 3000, described in connection to FIG. 3B, and may be designated "indicator hashtags." In one embodiment, the received set of indicator hashtags comprises a table of hashtags. At step 3180, the first and second sets of hashtags are compared to identify matches. In embodiments of step 3180, matches may be exact matches of hashtags (or hashkeys) or near matches (also referred to herein as close-enough matches). Near matches may be determined using Cosine, dot-product, or other similarity metrics. In some embodiments, a match or near match occurs where the hashes match and the indicator hashtag has a sig_ind of 1.

At step 3185, if the number of matches (hits) or near matches (near its) is at least one, then at step 3190 method 3100 recommends ordering the WGS or WES testing. In some embodiments, a recommendation is provided (such as visually via a graphical user interface) to a caregiver. In some embodiments, the testing orders may be automatically ordered. Additionally, in some embodiments where testing is carried out, the results may be used to update the first set of hashtags (as described in step 30080 of method 3000), which may be added to the second set of hashtags (indicator hashtags) for use in future runtime scenarios.

If there are no matches or near matches, then optionally at step 3195, for a random-sampling of target patients, WES or WGS testing may still be ordered. For example, in one embodiment, five percent of the patients may be tested even though a match was not determined. In this way, these embodiments of the invention may be enabled to continue to learn new potential combinations of markers that indicate actionable diagnoses.

At step 3199, if three are no matches or near matches, and random sampling is not performed, or following providing step 3190, method 3100 may stand down. In one embodiment, a healthcare computer program (which also may be embodied as a healthcare software agent, computer routine, or function) enters quiescence unless or until it is summoned again to perform method 3100.

Figure 7A:
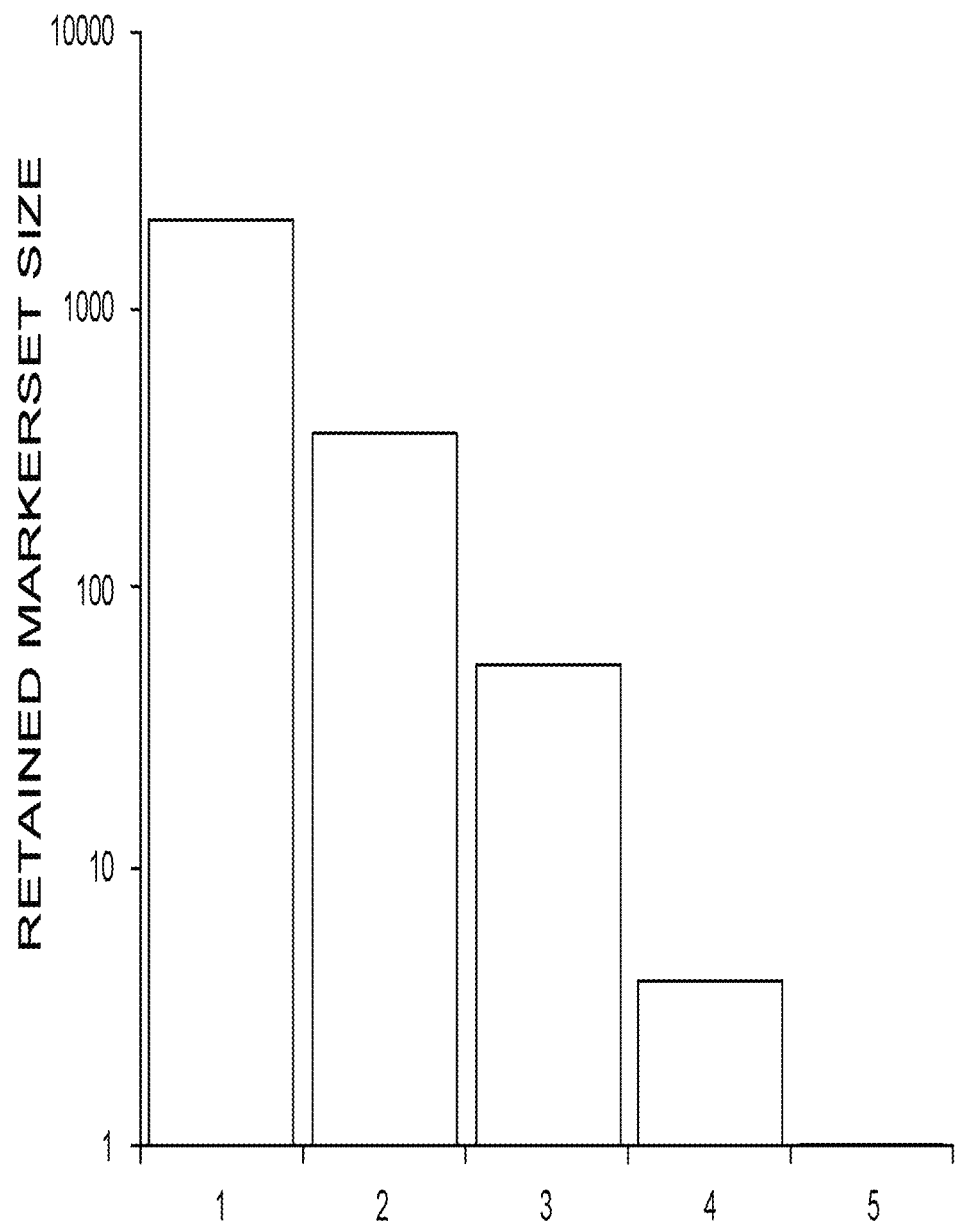
FIG. 7A illustratively depicts sensitivity to minimum count n11 setting for an example embodiment of the invention.

Returning briefly to FIG. 3A, embodiments of method 300 using BCPNN may be based on the calculation of an Information Component (IC). If Monte Carlo simulation is omitted, then the Bayesian model used may be the beta-binomial estimate of IC proposed by Bate and coworkers. If Monte Carlo simulation is performed, the model may be based on the Dirichlet-multinomial model. In some embodiments, the statistic for ranking the couples is the 2.5th percentile of the posterior distribution of the IC metric calculated by the Monte Carlo simulations. The value of the decision threshold and the minimum number of cases n11 required for a couple to be considered a candidate signal can both be adjusted to tune the sensitivity of the method to the prevalence of certain findings in the population. Sensitivity in the evaluation dataset was evaluated by setting the value of the threshold to a variety of integer values. Settings of n11 of 2, 3, 4, and 5 produced marker set sizes of 349, 53, 4, and, 1, respectively, as shown in FIG. 7A. If the value of n11 =1 and the decision threshold=1, then 2,104 couples are included and discrimination was reduced substantially.

Figure 7B:
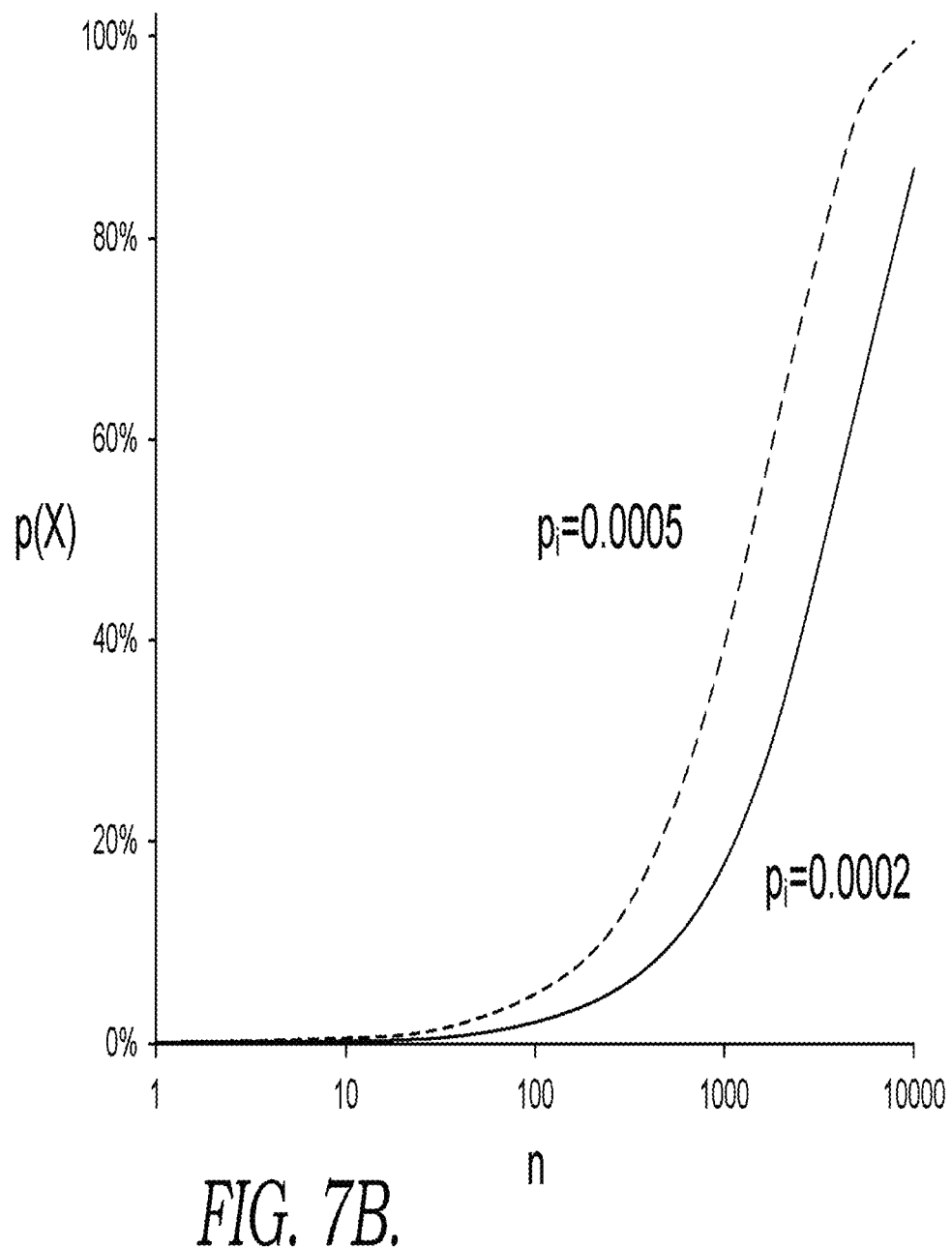
FIG. 7B illustratively depicts the probability of positive detection of at least one feature p(X) vs. number of dimensions or features n, for the purpose of pinpointing who WGS/WES is likely to benefit.

FIG. 7B illustrates why dimensionality (marker) reduction is important. In particular, where too many markers are included, then eventually 100% of the patient population would be determined positive for at least one feature and would then be routed forward the expensive WGS/WES testing. This the goal of some embodiments of the invention is to determine the number of markers n in order to pinpoint who WGS/WES is likely to benefit.

EXAMPLE

Example embodiments of our marker screener system and method and event surveillance system and method comprising an empirical Bayes confidence-propagation neural network (BCPNN), proportional reporting ratio (PRR), and Multi-item Gamma Poisson Shrinker (MGPS) methods and subsystems, has been reduced to practice. In this example embodiment, computer system 220, comprises a server cluster running the Linux operating system, software packages 226 comprises the open-source statistical software package R, the R modules PhViD version 1.0.3, e1071 (for the event surveillance example), cluster, and arules (for the event surveillance example) or arulesNBMIner (for the marker screener example), and the open-source BioConductor module LBE. Retrieval of structured discrete items was performed using Cerner's Discern Explorer™ operating on Cerner Millennium™ systems, one of which had been mapped using Cerner's Controlled Medical Terminology (CMT™) universal concept identifier ontology.

Regarding the marker screener example, data were extracted from a HIPAA-waivered, deidentified datawarehouse called Health Facts® which receives EHR (or EMR) data feeds on a nightly basis and contains a 100% sample of all episodes of care incident upon 616 U.S. acute care facilities. Single items and multi-item frequent marker sets were determined from a set of 102,483 transaction records. From these a total of 634 markers and 756 positive diagnoses were established, out of a total of 2,907 patients tested (26% positive). From these a total of 349 marker patterns were identified as statistically significantly associated with WES/WGS diagnostic yield by BCPNN.

Regarding the event surveillance example, the example embodiment has been validated by implementing it in high-mortality clinical contexts where conventional 'spontaneous adverse reports' are problematic due to sociological reasons of fear of medical malpractice litigation. In the context of in-patient care of acute myocardial infarction ("heart attack"), electronic medical record systems (EMRs) capture and store all of the transactions related to medication orders and meds administration and also automatically capture and store outcome occurrences electronically. Outcomes may include events or statuses that are observed and entered into the EMR by humans, such as patient expiry vs. patient discharge from the facility alive; however, many outcomes are ones such as laboratory test results and blood pressure and cardiac/hemodynamic parameters that are measured and electronically entered automatically, where humans do not enter but merely review the accumulating information.

With contemporary data warehouse computer systems comprised of EMR information, it is possible to automatically and continually perform data mining of all of the billions of transactions and events and statuses, classifying patterns that meet criteria that do constitute reportable adverse events of various types. It is not necessary that any human doctor or nurse or other person who is engaged in a patient's care notice the ADR-qualifying pattern and make the decision to write and file a spontaneous ADR. Indeed, embodiments of the present invention, including this example embodiment, are motivated (a) by the fact that ordinary human behavior leads to the present under-reporting of safety events, such that it is widely believed that less than 1% of adverse events that do occur are ever reported, and (b) by the consequent failure to detect the adverse events. Instead, embodiments of our invention operating as a data mining system connected to data feeds from a plurality of EMR systems detect the patterns and classify event types. This can include multivariable patterns and sequences that would be beyond the usual practical capabilities of humans to notice or that engender "separation of duties" related fragmentation of attention, especially when the prescriptions or interventions or other attributes that comprise the patterns are undertaken by a plurality of caregivers who may not be aware of what each is respectively doing (for example, the infectious disease doctor prescribing antibiotics for the patient may not bother to look at what medications the cardiologist is using for heart rhythm management or what medication the surgeon is using for preventing nausea and vomiting).

In all, it is routine that an acute myocardial infarction (AMI) patient may have 5 to 15 or more medications administered concomitantly. In the context of managing AMI, giving antiplatelet medication, analgesics, a beta-blocker, additional anti-hypertensives (such as an angiotensin converting enzyme (ACE) inhibitor, or an angiotensin receptor blocker (ARB), or a calcium channel blocker), a medication to help the patient sleep, a proton pump inhibitor (PPI) to prevent stomach ulceration, and an antiemetic are part of current best-practice standard of care. Chronic medications that treat pre-existing conditions that the patient has (such as diabetes, hypercholesterolemia, depression or other mental/behavioral conditions, epilepsy, etc.) are usually sustained throughout the hospital admission. Additionally, if the patient receives angioplasty/stenting (PCI) or coronary artery bypass grafting (CABG) surgery, perioperative antibiotics are prescribed; or, if post-operative infection supervenes, as is quite commonly the case, other antibiotics are used. If hypoperfusion or shock supervenes, still other medications (pressors, inotropes, loop diuretics, etc.) are added. And if abnormal heart rhythms develop, then antiarrhythmic medications are added.

Antiarrhythmic drugs that block the hERG receptor or potassium channel prolong the electrocardiogram QT interval and increase the risk for torsades de pointes, ventricular asystole, and cardiac death. Such drugs include amiodarone, dronedarone, sotalol, quinidine, procainamide, ibutilide, dofetilide, and disopyramide. Additionally, some macrolide and fluoroquinolone antibiotics, phenothiazine antipsychotics/antiemetics and SSRI antidepressants, serotonin agonists of the triptan class, cisapride, antiemetic 5-HT(3) inhibitors such as dolasetron and others have all been reported to also be associated with QT prolongation and cardiac arrhythmias Among these, the high likelihood of serious proarrhythmic effects of quinolone antibiotics has long been noted. Ciprofloxacin may be given to select patients because the agent is believed to be safer than levofloxacin, moxifloxacin, or other fluoroquinolone antibiotics, but such a belief is, to date, anecdotal and is not well-founded on evidence. Prolongation of the QT interval related to the effect of fluoroquinolones on rapid potassium channels (IKr) may lead to torsades de pointes and cardiac arrest (ventricular asystole).

Many cases of unexplained cardiac arrest temporally related to fluoroquinolone administration have appeared in the literature. Nonetheless, fluoroquinolones continue to be routinely utilized in acute care contexts where cardiac risk is already elevated, such as populations who are experiencing acute coronary syndrome (ACS) or AMI and are admitted to hospital for treatment. In the percutaneous coronary intervention (PCI) angioplasty/stenting and the coronary artery bypass grafting (CABG) subpopulation, these antibiotics continue to be commonly prescribed in care of such patients, even though there are alternative antibiotics that do not carry such risk of arrhythmias Furthermore, antibiotics with QT-prolonging side-effects are frequently prescribed in combination with amiodarone, ondansetron, SSRIs, antiepileptics, analgesics, and other medications that compound the risk of cardiac arrest.

Typically, a percentage of patients who are administered fluoroquinolone antibiotics develop marked QTc prolongation (QTc >550 msec) within 24 hours of antibiotic administration. Patients in whom such LQT syndrome develops may have genomic variants in one or more of the pathways involved in metabolizing and excreting the antibiotic or, in other instances, may be on one or more other concomitant medications that are either substrates or inhibitors of enzymes in those pathways, or, in yet other instances, may have comorbid organ system impairments that reduce the physiologic reserve that the organ systems possess to sustainably accommodate the incremental stresses that are placed upon them. Such drug-induced LQT patients tend to experience recurrent syncope, torsades de pointes requiring defibrillation, and other life-threatening hemodynamic and electrophysiologic abnormalities.

FIGS. 4A and 4B each show outcomes, provided in tables 400 and 450, respectively, of example applications of the example embodiment described above. In both example applications of the embodiment, herein referred to as Event Vigilence example A and Event Vigilence example B, data were extracted from a HIPAA-waivered, deidentified data warehouse, called Health Facts®, which receives EMR data feeds on a nightly basis and contains a 100% sample of all episodes of care incident upon 131 U.S. acute care facilities. For the period 01 Jan. 2008 through 31 Dec. 2010, an extraction produced a cohort of 6,699 patients admitted to hospital with AMI that was proven by troponin or creatine kinase MB tests and by electrocardiogram criteria who were between the ages of 35 and 60 years old; who survived at least 72 hours from the arrival at hospital; who had prior episodes of care with one or more measurements of LFTs had been performed wherein the LFT results had been in the normal range (less than the upper limit of normal ULN); and who received one or more measurements of LFTs during the index AMI admission. In this cohort there were 380 in-hospital deaths (5.7%) and 192 instances of LFT-ascertained Grade 4 liver injuries that materialized subsequent to drug exposure (2.9%).

Table 400 of FIG. 4A shows the results of the example embodiment's detection of statistical combinations of exposures (in this example, a drug or combinations of drugs) that were associated with increased relative risk of in-hospital patient death. Table 450 of FIG. 4B shows the results of the example embodiment's detection of statistically significant combinations of exposures (again in this example, a drug or combinations of drugs) that were associated with increased relative risk of developing in-hospital, life-threatening Grade-4 drug-associated liver injury. Ascertainment of the liver injury events was based on laboratory liver function test (LFT) results showing post-exposure increases (alanine aminotransferase ALT >20×ULN; or aspartate aminotransferase AST >20×ULN; or alkaline phosphatase ALKP >20× ULN; or total bilirubin TBIL >10×ULN) over pre-admission baseline values for the LFTs. Each row of tables 400 and 450, correspond to the results of an exposure. For example, row 401 provides results of patients who received Ciprofloxacin; row 402 shows the exposure combination of Amiodarone and Phenytoin, perhaps received by a patient having arrhythmia who also has epilepsy; row 455 shows the exposure combination of Ibuprofen and Levofloxacin. Rows 403 and 453 show the results of the entire cohort (in this example, the cohort, described above, of 6,699 patients admitted to hospital with AMI). Rows 403 and 453 thus provide a baseline mortality. For example, as shown in row 403, 380 patients of the 6,699 cohort (or 5.7%) died, and in row 453, 192 patients sustained irreversible Grade-4 liver injury. More specifically, in each instance, the 380 deaths and 192 incidents of injury are the numbers of patients among a total population of 6,699 AMI inpatients (ICD-9-CM 410.xx) admitted between 01 Jan. 2008 and 31 Dec. 2010 in 131 Cerner Health Facts® contributor institutions, subset of patients who (a) remained alive for length of stay >72 hours, (b) who had one or more ALT, AST, ALKP, and/or TBIL measurements subsequent to the time when the index medication was dispensed, and (c) had one or more values for each of ALT, AST, ALKP, and TBIL in the normal range during episodes of care prior to the index AMI admission. The total 6,699 serves as reference for calculation of relative risk (RR).

Columns 405 and 455 indicate the particular candidate exposure, such as the drug or combination of drugs, being evaluated against the cohort. Columns 410 and 460 show the number of patients who received the exposure; for example, in column 410 of table 400, 386 patients (or 5.8% of the 6,699 cohort) received Ciprofloxacin. Columns 415 and 465 show the actual number of patients, out of the 6,699 cohort, who died (415) or sustained Grade-4 liver injury (465). Columns 420 and 470 show the expected number of patients, out of the 6,699 cohort, who died (420) or sustained Grade-4 liver injury (470). Columns 425 and 475 show a relative risk or likelihood of dying, where the overall population (the cohort of 6,699 patients) is given a value of 1.0. For example, if a particular patient in this cohort would otherwise have a 5.7% chance of dying, and now that patient is given Ciprofloxacin (row 401), then that patient's risk of dying goes up to 33.4% or 5.9 times more likely to die. Thus, while the expected number of deaths (column 420) is only 28.3, the example embodiment shows that the actual number of deaths (column 415) is 129. A surgeon or cardiologist might otherwise prescribe Ciprofloxacin as a peri-operative to prevent infection, unaware of the risk to the patient or that the patient dies several days later.

Continuing with FIGS. 4A and 4B, columns 430 and 480 show the ratio of actual vs. expected number of deaths or sustained Grade-4 liver injuries. Columns 435 and 485 show the determined P-value, such as the P-value described above in connection to method 300 of FIG. 3. In this example embodiment, a Bayesian confidence propagation neural network (BCPNN) algorithm, Empirical Bayes (EB) algorithm, and Gamma Poisson Shrinker algorithm were used for signal detection and p-value calculation. The top 200 medications were extracted from Health Facts® data warehouse. Medications or combinations of concomitant medications with fewer than ten patient exposures to the combo were omitted from the analysis. Medications or combinations of concomitant medications with fewer than three events were omitted from the analysis. A Monte Carlo simulation burn-in comprising 2,000 iterations, followed by 50,000 iterations was applied to produce the expected number counts (columns 420 and 470) and p-values (columns 435 and 485). Columns 440 and 490 show the 'number-needed-to-harm' or NNH, as described above, for each exposure of interest.

Our example event surveillance system and method embodiment discovered 14 exposures (FIG. 4A) that were associated with statistically significant (p <0.05) increased risk of in-hospital mortality, elevated up to 5.9-fold above the mortality risk experienced by the cohort as a whole. It discovered six exposures (FIG. 4B) that were associated with up to 5.3-fold increased risk of Grade-4 liver injury while the patients were in-hospital.

All of the medications in this example are drugs that have been on the market for a relatively long time, so it was possible to validate the signals detected in the 2008-2010 inpatient AMI cohort by comparing to data extracted for the 7,103-patient inpatient AMI cohort from the de-identified EMR-derived records incident upon the same institutions participating in the Cerner Health Facts® data warehouse during the period 01 Jan. 2005 through 31 Dec. 2007. The same signals were identified in the 2005-2007 cohort, at approximately the same p-value significance levels. This example scenario reveals that there are several clinically-important and heretofore-unrecognized exposures of AMI patients to individual medications and combinations of medications that are unsafe, in terms of significantly increased risk of mortality and/or life-threatening drug-associated liver injury.

This finding is important not only with regard to the fact that none of the manufacturers of the drugs involved, nor the national regulatory agencies, have previously identified these safety signals in human-submitted spontaneous adverse drug reaction (ADR) reports, and therefore have evidently failed to prevent injury and death because of false-negative errors and inability to detect such signals in the sparse spontaneous ADR submissions. The finding is also important insofar as it illustrates (a) the profound improbability of conventional prior art systems and of current practices implemented by regulators and manufacturers, to detect important patterns that involve second- or higher-order combinations of exposures that are outside the purview and responsibility of any one manufacturer or any one therapeutic product, and (b) the previously under-appreciated way in which relatively common comorbid conditions confer disproportionate risks on certain subsets of the population (e.g., people who develop a sequelae or complications (for example, arrhythmias) secondary to or comorbid with the index context (for example, AMI); people with epilepsy who are on anticonvulsant medications; people with depression or psychosis who are on antidepressant or antipsychotic medications). The example reveals that one serious acute condition, such as AMI, can create a clinical and pharmacotoxicologic context wherein a drug that is ordinarily safe and effective in a healthier population in which the drug is labeled for use can become unsafe to use, at least in the routinely prescribed forms and dosages. The example highlights how prior art and conventional systems and methods that entail diluted, aggregated populations pooling a predominant percentage of people who do not have that condition with a modest percentage of people who do have the condition, can result in failure to detect a signal (false-negative Type II statistical error). Further, it reveals how components of routine standing-orders and order-sets and protocols (e.g., NSAID analgesics; periop- erative antibiotics; 5-HT(3) inhibitor or phenothiazine antiemetics) that are conventionally regarded as very safe and, thus, are prescribed in a de rigeur, uncritical fashion can, given the right context and concomitant second- or higher-order combinations of factors, become distinctly unsafe in-context, in a manner that doctors, regulators, and manufacturers would all have difficulty detecting without the assistance of embodiments of the invention.

Turning now to FIGS. 5A and 5B, a portion of results from the application of the actual reduction to practice of the embodiment described above in connection to FIGS. 4A and 4B, is provided in table 500, which is shown across FIGS. 5A and 5B. In table 500, each row, such as row 501 shows information of an exposure of interest (column 505), such as a drug or combination of drugs. As described above, this example application uses a cohort of 6,699 AMI inpatients admitted between 01 Jan. 2008 and 31 Dec. 2010 in 131 Cerner Health Facts® contributor institutions, who (a) remained alive for length of stay >72 hours, (b) who had one or more ALT, AST, ALKP, and/or TBIL measurements subsequent to the time when the index medication was dispensed, and (c) had one or more values for each of ALT, AST, ALKP, and TBIL in the normal range during episodes of care prior to the index AMI admission. Column 510 shows the number of patients who received the exposure of interest (column 505). Column 515 shows the exposure prevalence or percentage of the total 6,699 population who were exposed to the drug or drug combination; thus, for example, 76.4% (or 5120) of the 6,699 patients received acetaminophen, suggesting that prescribing acetaminophen is a common procedure for patients belonging to the reference population (i.e. the 6,699 patients of the cohort). Columns 520, 525, 530, 535, and 540 show the count of adverse events resulting from the exposure. Here, AE1 of column 520 shows in-house morality, as a count and also as a percentage of the count from the number receiving exposure (column 510); AE2-AE5 (columns 525, 530, 535, and 540, respectively) show the count for grade 1-4 liver injuries. Column 545 shows the percentage of Grade-4 liver-injury count (column 540) from the number receiving exposure (column 510).

Example results indicating likely qualifying signals can be observed in items 521 and 523, in column 520, of Table 500. Items 521 and 523 are specific values of in-house mortality parentages, where 521 shows higher percentages (8.6%, 10.1%, and 13.5%) than the 5.7% of the cohort that died, while 523 shows a lower percentage 3.4%, indicating here that patients of this cohort may be less likely to die when exposed to atorvastatin.

Continuing with table 500, in FIG. 5B, column 560 shows the total negative exposed count (i.e. the total population of the cohort (6,699) minus the number receiving exposure (column 510)). The columns of 570 and 580 represent metrics associated with mortality and Grade-4 liver injury, respectively. Columns 571 and 581 show the count of patients who received exposure to the drug or exposure of interest who died (column 520) or sustained grade-4 liver injury (column 540). Columns 572 and 582 show the count of patients who were exposed to the drug (or exposure of interest) who did not die (i.e. column 572 equals column 510 minus column 571) or sustain Grade-4 liver injury (i.e. column 582 equals column 510 minus column 581). Columns 573 and 583 show the count of patients who were not exposed to the drug (or exposure of interest) and who died (column 573 equals the total number of patients in the cohort who died (380) minus column 571) or sustained Grade-4 liver injury (column 583 equals the total number of patients in the cohort who sustained Grade-4 liver injury (192) minus column 581). Columns 574 and 584 show the count of patients who were not exposed to the drug (or exposure of interest) and who did not die (column 574 equals column 560 minus column 573) or did not sustain Grade-4 liver injury (column 584 equals column 560 minus column 583). Finally, columns 576 and 586 show NNT1 for mortality and NNT2 for Grade-4 liver injury, respectively, and columns 578 and 588 show NNH1 for mortality and NNH2 for Grade-4 liver injury, respectively. In this example NNT1 can be determined as: 1/([column 510]—[column 571]/[column 510]—([column 560]-[column 573])/[column 560]), where NNT1 is not less than zero. NNT2 of column 586 can be determined similarly using columns 581 and 583 in place of 571 and 573, respectively.

NNH1 can be determined as: 1/([column 571]/[column 510]-[column 573]/ [column 560]), where NNH1 is not less than zero. NNH2 of column 588 can be determined similarly using columns 581 and 583 in place of 571 and 573, respectively. Finally, columns 596 and 598 provide ratios of NNT to NNH for assessing the balance of probable benefits and harms, as described above.

ADDITIONAL EXAMPLE EMBODIMENTS

Additional example embodiments include: A system, method, and computer readable media are provided for discovering and validating latent relationships in a dataset, including pharmacovigilance data, medical device vigilance data, or therapeutic procedures and services data, comprising: (i) determining a sample size-independent measure of association between two conditions of interest in the dataset of pharmacovigilance data on a suitably programmed computing device; (ii) analyzing a hypergeometric distribution to determine a measure of statistical unexpectedness between the conditions of interest in said dataset on a suitably programmed computing device, wherein said distribution is based on an urn model under a hypothesis that said conditions are statistically independent; and (c) displaying the measure of association with the measure of the statistical unexpectedness to identify, a significant association between the conditions of interest on a suitably programmed computing device, and involving: (a) obtaining or extracting the records and/or documents (corpora) from a plurality of source record-keeping systems or computer databases; (b) selecting the raw data for a plurality of variables, together with demographic and clinical attributes associated with the cases from the episodes of care that were associated with each data item; (c) establishing for any particular candidate group of patients having exposure to a therapeutic (or therapeutic "combo" or "sequence") of interest, one or more corresponding 'reference' or 'comparator' populations whose attributes are statistically well-matched to those of the candidate group; and (d) omitting to include exposure combination-event vectors that have zero counts or, more preferably, that have fewer than 3 counts that have been accessioned during the relevant time period that is the subject of analysis. In some embodiments the measure of association is a relative risk or an odds ratio.

The system, method, and computer readable media described above, wherein the dataset comprises binary data (such as data with values of yes or no, true or false, "1" or "zero", for example) and the measure of association comprises a reporting ratio such as PRR, or BCPNN p-value, or MGPS p-value, or similar measures of relative risk and significance. Furthermore, in some embodiments, the significant association between the conditions of interest is determined if the NNH is small, generally less than 30, or if the balance of likely benefit and harm for the conditions of interest, as reflected by the ratio NNT/NNH, is significantly greater than 1 and the seriousness and probability of likely harm exceeds the magnitude and probability of the likely benefit that can be expected by undertaking the pattern of therapeutic actions. In some embodiments, the significance threshold is adjusted for multiple comparisons, and in some embodiments, the significance threshold is adjusted using an algorithm to estimate the False Discovery Rate (FDR), such as the Benjamini-Hochberg algorithm, wherein the significance threshold is adjusted to θ/M where M represents the number of comparisons between the first and second conditions of interest.

Furthermore, in some embodiments of the system, method, and computer readable media described above, the first condition of interest is a fixed reference condition, and the second condition of interest is at least one relevant comparison condition or population. Still further, in some embodiments, the first condition of interest is a presence of a drug and the second condition of interest is an adverse event.

In some embodiments of the system, method, and computer readable media described above, displaying the measure of association comprises separately indicating negative associations with reporting ratios less than one from positive associations with reporting ratios greater than one, and in some embodiments, displaying the measure of association comprises displaying statistically significant absent conditions in which NAB=0.

In some embodiments of the system, method, and computer readable media described above, the dataset is partitioned into one or more subsets, and steps (a) through (c) are performed on each subset. In some embodiments the step of partitioning the dataset into subsets comprises partitioning into fixed size moving window partitions based on an index of records in the dataset or on one or more fields in the records in the dataset. In some embodiments, these fields in the records comprise one of a reporting date, a gender, or an age. In some embodiments, the step of partitioning the dataset into subsets comprises using a nearest neighbor partitioning which applies a distance function to the one of more fields in the records in the dataset, and in some embodiments, the step of partitioning the dataset comprises using cluster based partitioning. In some embodiments, the corresponding measures of association displayed as points from the corresponding subsets of data are visually linked together using vectors. In some embodiments, the measure of association and the statistical unexpectedness for each subset is plotted on a graph as a trajectory in which the variations across the subsets are indicative of variations in time or dosage. In some embodiments, the subsets indicate data collected over time, and in some embodiments, the measure of association is tracked longitudinally while the measure of statistical unexpectedness may decrease, increase, or remain constant over time.

Some embodiments of the system, method, and computer readable media described above further comprises combining the first and second conditions of interest, when a significant association between the first and second conditions of interest is determined, as a new fixed first condition of interest, and repeating steps (a)-(c) with a third condition of interest represented as a new second condition of interest. Further, in some embodiments, the new first condition of interest is a combination of a drug and an adverse event while the new second condition of interest is another drug. Some embodiments further comprise constructing and plotting the conditions of interest while the partitioning step varies partitions based on selecting different fields and/or values of fields used for partitioning the dataset into subsets.

In some embodiments of the system, method, and computer readable media described above, the step of determining a significant association comprises using likelihood-of-association information from a medical and biological database. Further, in some embodiments, the biological or medical databases comprise information from biological pathways affected by each drug, encoded in the form of a numerical vector.

In some embodiments of the system, method, and computer readable media described above, pairs of a first condition and a second condition include one among a particular drug and a second drug taken with the particular drug, or a first adverse event and a second adverse event that occurs with the first adverse event.

Some embodiments of the system, method, and computer readable media described above further comprise (1) taking a number of samples from the dataset; (2) recalculating the reporting ratio and the measure of unexpectedness for each of the number of samples; and (3) displaying a confidence box around an adverse event based on corresponding points for that adverse event for each of the calculated and recalculated reporting ratios and the measure of unexpectedness for each of the number of samples. Further, in some embodiments, each of the samples contain between 40-80% of the records in the database, and in some embodiments, each of the samples are selected to eliminate records containing a certain percentage of drugs in the dataset.

In some embodiments of the system, method, and computer readable media described above, the measure of association is displayed using color coded values indicative of either the data underlying the particular association or a significance of the association.

Some embodiments of the system, method, and computer readable media described above further comprise (I) taking a number of samples from the dataset; (II) recalculating and displaying as points the reporting ratio and the measure of unexpectedness for each of the number of samples; and (III) displaying points corresponding to the same pair of conditions across the number of samples in an integrated display by a vector.

Additional embodiments include a system comprising a central processing unit and memory containing logic (CPU) for analyzing a dataset of EMR-derived data, comprising: (a) an input data feed for extracting and transferring the dataset of pharmacovigilance data; (b) a processing unit configured to: (i) determining a sample size-independent measure of association between two or more conditions of interest in the dataset of pharmacovigilance data; and (ii) analyzing a the data to determine a measure of statistical unexpectedness between the conditions of interest in said dataset; and (c) a display unit for displaying the measure of association with the measure of the statistical unexpectedness to identify a significant association between the conditions of interest.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

Accordingly, in one aspect one or more computer-readable media are provided, the media having computer-usable instructions embodied thereon that, when executed, enable a given processor to perform a method for discovering and validating latent relationships in a dataset including pharmacovigilance data, medical device vigilance data, or therapeutic procedures and services data. The method includes receiving target information associated with a target population of patients from a first set of records of a first health-records system; receiving reference information associated with a reference population of patients from a second set of records of a second health-records system; receiving exposure information specifying an exposure of interest; determining frequent item-sets associated with the target population; receiving first raw data from the target information associated with the target population comprising a first plurality of instances associated with the specified exposure of interest; receiving second raw data from the reference information associated with the reference population comprising a second plurality of instances statistically well matched to the first plurality of instances of the first raw data; performing cluster-based matching of the first and second raw data to determine one or more clusters; determining at least one measure quantifying difference for at least one cluster; and comparing the measure to a first predetermined threshold to create a provisional binding of one or more of the first plurality of instances to the exposure of interest.

In some embodiments, the method further includes determining a false discovery rate of the measure to determine a second measure; and comparing the second measure to a second predetermined threshold to create a provisional binding of one or more of the first plurality of instances to the exposure of interest. In some embodiments, the false discovery rate is determined using a Benjamini-Hochberg algorithm. In some embodiments, the receiving first raw data from the target information comprises receiving records containing demographic attributes associated with episodes of care that are associated with the data item. In some embodiments, the statistically well matched instances comprises a matching among one or more demographic attributes associated with the target information of the first set of records to one or more demographic attributes associated with the reference information of the second set of records. In some embodiments, the determining at least one measure quantifying difference comprises using a Bayesian Confidence Propagation Neural Network algorithm. In some embodiments, the determining at least one measure quantifying difference comprises using a Bayesian Confidence Propagation Neural Network algorithm and at least one of a proportional reporting ratio algorithm, Empirical Bayes algorithm, and a Multi-item Gamma Poisson Shrinker algorithm. In some embodiments, the measure determined using the Bayesian Confidence Propagation Neural Network algorithm is compared with each measure determined using the at least one of the a proportional reporting ratio algorithm, Empirical Bayes algorithm, and a Multi-item Gamma Poisson Shrinker algorithm. In some embodiments, the cluster-based matching is based on demographic attributes associated with the first and second raw data.

In another aspect, a method is provided for discovering latent relationships in data. The method includes receiving target information associated with a target population of patients from a first set of records of a first health-records system; receiving reference information associated with a reference population of patients from a second set of records of a second health-records system; receiving exposure information specifying an exposure of interest; determining frequent item-sets associated with the target population; receiving first raw data from the target information associated with the target population comprising a first plurality of instances associated with the specified exposure of interest; receiving second raw data from the reference information associated with the reference population comprising a second plurality of instances statistically well matched to the first plurality of instances of the first raw data; performing cluster-based matching of the first and second raw data to determine one or more clusters; determining at least one measure quantifying difference for at least one cluster; and comparing the measure to a first predetermined threshold to create a provisional binding of one or more of the first plurality of instances to the exposure of interest.

In some embodiments, the method further includes determining a false discovery rate of the measure to determine a second measure; and comparing the second measure to a second predetermined threshold to create a provisional binding of one or more of the first plurality of instances to the exposure of interest. In some embodiments, the receiving first raw data from the target information comprises receiving records containing demographic attributes associated with episodes of care that are associated with the data item. In some embodiments, the statistically well matched instances comprises a matching among one or more demographic attributes associated with the target information of the first set of records to one or more demographic attributes associated with the reference information of the second set of records. In some embodiments, the determining at least one measure quantifying difference comprises using a Bayesian Confidence Propagation Neural Network algorithm. In some embodiments, the determining at least one measure quantifying difference comprises using a Bayesian Confidence Propagation Neural Network algorithm and at least one of a proportional reporting ratio algorithm, Empirical Bayes algorithm, and a Multi-item Gamma Poisson Shrinker algorithm. In some embodiments, the measure determined using the Bayesian Confidence Propagation Neural Network algorithm is compared with each measure determined using the at least one of the a proportional reporting ratio algorithm, Empirical Bayes algorithm, and a Multi-item Gamma Poisson Shrinker algorithm. In some embodiments, the cluster-based matching is based on demographic attributes associated with the first and second raw data.

In yet another embodiment, a computer program product is provided, the computer program product residing on a computer readable storage medium that, when executed on a computing system, analyzes a dataset of pharmacovigilance data. The program product includes code for determining a measure of association between two conditions of interest in the dataset of pharmacovigilance data, wherein the measure is sample size-independent; code for determining, from the dataset, a measure of statistical unexpectedness; and code for displaying the measure of association with the measure of the statistical unexpectedness to facilitate identifying an association between an exposure and one or more condition(s) of interest. In some embodiments, the measure of statistical unexpectedness is determined as one of a probability value. And, in some embodiments, the computer-program product further comprises code for determining a False Discovery Rate of the measure of statistical unexpectedness.

In yet another aspect, a method is provided for discovering and validating latent relationships in data, including diagnostic data. The method comprises: (a) determining a sample size-independent measure of association between two conditions of interest in the dataset of phenotypic diagnostic data on a suitably programmed computing device; (b) analyzing a hypergeometric distribution to determine a measure of statistical unexpectedness or phenotypic influence on the diagnostic yield for a genomics-oriented diagnostic test, such as sequencing or microarray testing, between the conditions of interest in said dataset on a suitably programmed computing device, wherein said distribution is based on a model under a hypothesis that said conditions are statistically independent; (c) displaying the measure of association with the measure of the statistical unexpectedness to identify, a significant association between the conditions of interest on a suitably programmed computing device; (d) undertaking genomics testing in selected individuals as determined by their phenotypic diagnostic data in relation to the measures of association of the phenotypic data to diagnostic yield of the genomics tests; (e) diagnosing a genetic condition in a proband. In some embodiments, the method further comprises: (i) obtaining or extracting the records and/or documents (corpora) from a plurality of source record-keeping systems or computer databases; (ii) selecting the raw data for a plurality of variables, together with demographic and clinical attributes or conditions associated with the cases from the episodes of care that were associated with each data item; (iii) establishing for any particular candidate group of patients having exposure to a diagnostic test of interest, one or more corresponding 'reference' or 'comparator' populations whose attributes are statistically well-matched to those of the candidate group; (iv) by a processor and from a list of phenotypic variants, removing variants that are present in unaffected controls above a specified frequency and specified occurrence that are determined by the input; (v) by a processor omitting to include exposure combination-diagnostic status vectors that have zero counts or, more preferably, that have fewer than 3 counts that have been accessioned during the relevant time period that is the subject of analysis; and (vi) by a processor, identifying the diagnostic-yield grouping of which an individual patient is a member based on a clustering algorithm applied to one or more remaining variants in the list.

In some embodiments of the method, the dataset comprises binary data and the measure of association comprises a reporting ratio such as PRR, or BCPNN p-value, or MGPS p-value, or other measures of relative risk and significance such as are known to those practiced in the art. In some embodiments of the method, the first condition of interest is a fixed reference condition, and the second condition of interest is at least one but more usually a plurality of relevant comparison conditions or populations. In some embodiments of the method, the first condition of interest is a presence of a drug and the second condition of interest is an adverse event. Further, in some embodiments, a significance threshold is adjusted for multiple comparisons, and in particular, in the significance threshold may be adjusted using an algorithm to estimate the False Discovery Rate (FDR), such as the Benjamini-Hochberg algorithm wherein the significance threshold is adjusted to $\theta/M$ where M represents the number of comparisons between the first and second conditions of interest.

In some embodiments of the method, displaying the measure of association comprises separately indicating negative associations with reporting ratios less than one from positive associations with reporting ratios greater than one; and/or displaying the measure of association comprises displaying statistically significant absent conditions in which NAB=0.

In some embodiments, the method further includes partitioning the dataset into subsets and performing steps (a)-(c) for each subset of the dataset. In some embodiments, the step of partitioning the dataset into subsets comprises partitioning into fixed size moving window partitions based on an index of records in the dataset or on one or more fields in the records in the dataset. In some embodiments, the fields in the records comprise one of a reporting date, a gender, or an age, and in some embodiments, the step of partitioning the dataset into subsets comprises using a nearest neighbor partitioning which applies a distance function to the one of more fields in the records in the dataset. In some embodiments, the step of partitioning the dataset comprises using cluster based partitioning.

In some embodiments, the method further includes combining the first and second conditions of interest, when a significant association between the first and second conditions of interest is determined, as a new fixed first condition of interest and repeating steps (a)-(c) with a new second condition of interest. In some embodiments, the new first condition of interest is a combination of a drug and an adverse event while the new second condition of interest is another drug. In some embodiments, the method further includes constructing and plotting conditions of interest while the partitioning step varies partitions based on selecting different fields and/or values of fields used for partitioning the dataset into subsets. In some embodiments, the step of determining significant associations comprises using likelihood-of-association information from other medical and biological databases.

In some embodiments, the method further include (a) taking a number of samples from the dataset; (b) recalculating the reporting ratio and the measure of unexpectedness for each of the number of samples; and (c) displaying a confidence box around an adverse event based on corresponding points for that adverse event for each of the calculated and recalculated reporting ratios and the measure of unexpectedness for each of the number of samples. In some embodiments, each of the samples contain between 40-80% of the records in the database, and/or in some embodiments, each of the samples are selected to eliminate records containing a certain percentage of drugs in the dataset. In some embodiments, the measure of association is displayed using color coded values indicative of either the data underlying the particular association or a significance of the association. Further, in some embodiments, corresponding measures of association displayed as points from the corresponding subsets of data are visually linked together using vectors.

In some embodiments, the method further include (a) taking a number of samples from the dataset; (b) recalculating and displaying as points the reporting ratio and the measure of unexpectedness for each of the number of samples; and (c) displaying points corresponding to the same pair of conditions across the number of samples in an integrated display by a vector. In some embodiments, the measure of association and the statistical unexpectedness for each subset is plotted on a graph as a trajectory in which the variations across the subsets are indicative of variations in time or dosage. In some embodiments, the subsets indicate data collected over time, and wherein if the measure of association is tracked longitudinally while the measure of statistical unexpectedness may either decrease, increase, or remain constant over time.

In some embodiments, the assaying is sequencing, and the sequencing comprises a sequencing method selected from the group consisting of Whole Exome Sequencing (WES), Massively Parallel Signature Sequencing (MPSS), polony sequencing, 454 pyrosequencing, Illumina sequencing, SOLiD sequencing, ion semiconductor sequencing, DNA nanoball sequencing, heliscope single molecule sequencing, single molecule real time (SMRT) sequencing, RNAP sequencing, Nanopore DNA sequencing, sequencing by hybridization, or Sanger-type microfluidic Whole Genome Sequencing (WGS). Further, in some embodiments, the nucleic acid sample is collected from blood, saliva, urine, serum, tears, skin, tissue, or hair from the subject. Still further, in some embodiments, the assaying the nucleic acid sample from the subject comprises purifying polynucleotides from the nucleic acid sample; and directly assaying one or more of the purified polynucleotides, amplifying a nucleotide sequence of the purified polynucleotides, or performing a microarray analysis of the purified polynucleotides. Further still, in some embodiments, the assaying is microarray analysis, and wherein the microarray analysis comprises a Comparative Genomic Hybridization (CGH) array analysis, a gene expression analysis, or an SNP array analysis.

In some embodiments, the method further includes determining whether the subject has the developmental disorder or the altered susceptibility to the developmental disorder. In some embodiments, the subject (patient) was previously diagnosed or is suspected as having the developmental disorder or the altered susceptibility to the developmental disorder based on an evaluation by a psychologist, a neurologist, a psychiatrist, a speech therapist, a pediatrician, or other professional who screens subjects for developmental disorders. In some embodiments, the determining comprises an evaluation of the subject's communication, socialization, cognitive abilities, body movements, family history of developmental or psychiatric disorders, or a combination thereof. In some embodiments, the clustering method is one of k-means clustering, Expectation-Maximization distribution-based clustering, density-based clustering, kernel-based clustering, spectral clustering, sequence clustering, subspace clustering, or projected clustering.

In yet another aspect, a system is provided comprising: one or more central processing units (CPU) for analyzing a dataset of EMR-derived data, (a) an input data feed for extracting and transferring the dataset of phenotypic data; (c) one or more computer storage media storing computer-useable instructions that, when executed by the one or more processors, implement a method comprising: (i) determining a sample size-independent measure of association between two or more conditions of interest in the dataset of pharmacovigilance data; and (ii) analyzing a the data to determine a measure of statistical unexpectedness between the conditions of interest in said dataset; and (c) a display unit for displaying the measure of association with the measure of the statistical unexpectedness to identify a significant association between the conditions of interest.

In yet another aspect, a computer program product is provided on a computer readable storage medium that, when executed on a computing system, analyzes a dataset of phenotypic data, the program product comprising: (a) code for determining a sample size-independent measure of association between two conditions of interest in the dataset of phenotypic data; (b) code for analyzing the data to determine a measure of statistical unexpectedness, such as a probability or p-value; and (c) code for displaying the measure of association with the measure of the statistical unexpectedness to identify a significant association between the exposure and the condition(s) of interest.

In some embodiments, further comprising analyzing a dataset, the program product comprising code for determining the False Discovery Rate (FDR), thereby to control the possibility for false-positive (Type I) statistical errors in interpreting the results. In some embodiments, further comprising determining a diagnostic plan based on the phenotypic influence on diagnostic yield.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computer-implemented method for generating a recommendation to conduct whole genome sequencing or whole exome sequencing (WGS/WES) testing on a human patient based on a likelihood of receiving an actionable diagnosis, the method comprising:
    filtering a first plurality of electronic health records (EHR) utilizing one or more marker code combinations to identify an EHR for a patient including at least one phenotypic feature combination corresponding to at least one marker code combination of the one or more marker code combinations; and
    generating a recommendation for administration of a WGS/WES test in a EHR for each of the first plurality of EHRs including at least one phenotypic feature combination corresponding to at least one marker code combination of marker code combinations;
        wherein the one or more marker code combinations generated by encoding machine readable code combination sets from a table of clinical codes representative of phenotypic features extracted from a second plurality of EHRs that include a diagnosis made or confirmed based on the results of the WGS/WES testing, the clinical codes generated such that a particular clinical code is representative of at least one phenotypic feature but any particular phenotypic feature is represented by no more than one clinical code, and computing, using a neural network or Multi-item Gamma Poisson Shrinker, the one or more marker code combinations as having a probability greater than a predetermined threshold from the machine readable code combination sets.

2. The computer-implemented method of claim 1, further comprising presenting the recommendation as a visual alert within a user interface.

3. The computer-implemented method of claim 2, further comprising automatically scheduling, using a healthcare computer program associated with the EHR for the patient, WES/WGS testing for the human patient based on the determine likelihood.

4. The computer-implemented method of claim 1, wherein code combination set comprises up to five clinical codes.

5. The computer-implemented method of claim 1, wherein identifying at least one clinical code or combination of at least two clinical codes comprises determining a near match with the marker code combination set using cosine or dot-product.

6. The computer-implemented method of claim 1, further comprising diagnosing a genetic condition in a proband.

7. The computer-implemented method of claim 1, further comprising analyzing a hypergeometric distribution to determine a measure of statistical unexpectedness or phenotypic influence on the diagnostic yield for a genomics-oriented diagnostic test.

8. The computer-implemented method of claim 7, wherein analyzing a hypergeometric distribution to determine a measure of statistical unexpectedness or phenotypic influence on the diagnostic yield for a genomics-oriented diagnostic test comprises sequencing or microarray testing, between the conditions of interest in the dataset.

9. One or more computer-readable media having computer-usable instructions embodied thereon that, when executed by a computer processor, enable the computer processor to perform a method for generating a recommendation to conduct whole genome sequencing or whole exome sequencing (WGS/WES) testing on a human patient based on a likelihood of receiving an actionable diagnosis, the method comprising:
    filtering a first plurality of electronic health records (EHR) utilizing one or more marker code combinations to identify an EHR for a patient including at least one phenotypic feature combination corresponding to at least one marker code combination of the one or more marker code combinations; and
    generating a recommendation for administration of a WGS/WES test in a EHR for each of the first plurality of EHRs including at least one phenotypic feature combination corresponding to at least one marker code combination of marker code combinations;
        wherein the one or more marker code combinations generated by encoding machine readable code combination sets from a table of clinical codes representative of phenotypic features extracted from a second plurality of EHRs that include a diagnosis made or confirmed based on the results of the WGS/WES testing, the clinical codes generated such that a particular clinical code is representative of at least one phenotypic feature but any particular phenotypic feature is represented by no more than one clinical code, and computing, using a neural network or Multi-item Gamma Poisson Shrinker, the one or more marker code combinations as having a probability greater than a predetermined threshold from the machine readable code combination sets.

10. The computer-readable media of claim 9, wherein identifying at least one clinical code or combination of at least two clinical codes comprises determining a near match with the marker code combination set using cosine or dot-product.

11. The computer-readable media of claim 9, further comprising automatically scheduling the patient for the WGS/WES testing using a healthcare computer program.

12. The computer-readable media of claim 11, wherein the healthcare computer program comprises a healthcare software agent.

13. The computer-readable media of claim 9, further comprising presenting the recommendation as a visual alert within a user interface.

14. The computer-readable media of claim 9, further comprising automatically scheduling, using a healthcare computer program associated with the EHR for the patient, WES/WGS testing for the human patient based on the determine likelihood.

15. The computer-readable media of claim 9, further comprising diagnosing a genetic condition in a proband.

16. The computer-readable media of claim 9, further comprising analyzing a hypergeometric distribution to determine a measure of statistical unexpectedness or phenotypic influence on the diagnostic yield for a genomics-oriented diagnostic test.

17. The computer-readable media of claim 9, wherein analyzing a hypergeometric distribution to determine a measure of statistical unexpectedness or phenotypic influence on the diagnostic yield for a genomics-oriented diagnostic test comprises sequencing or microarray testing, between the conditions of interest in the dataset.

18. A method for generating a recommendation to conduct whole genome sequencing or whole exome sequencing (WGS/WES) testing on a human patient based on a likelihood of receiving an actionable diagnosis, the method comprising:

filtering a first plurality of electronic health records (EHR) utilizing one or more marker code combinations to identify an EHR for a patient including at least one phenotypic feature combination corresponding to at least one marker code combination of the one or more marker code combinations; and generating a recommendation for administration of a WGS/WES test in a EHR for each of the first plurality of EHRs including at least one phenotypic feature combination corresponding to at least one marker code combination of marker code combinations;

wherein the one or more marker code combinations generated by encoding machine readable code combination sets from a table of clinical codes representative of phenotypic features extracted from a second plurality of EHRs that include a diagnosis made or confirmed based on the results of the WGS/WES testing, the clinical codes generated such that a particular clinical code is representative of at least one phenotypic feature but any particular phenotypic feature is represented by no more than one clinical code, and computing, using a neural network or Multi-item Gamma Poisson Shrinker, the one or more marker code combinations as having a probability greater than a predetermined threshold from the machine readable code combination sets.

19. The method of claim 18, further comprising analyzing a hypergeometric distribution to determine a measure of statistical unexpectedness or phenotypic influence on the diagnostic yield for a genomics-oriented diagnostic test.

20. The method of claim 18, further comprising performing genomics testing in selected individuals according to their phenotypic diagnostic data in relation to the measures of association of the phenotypic data to diagnostic yield of the genomics tests.

* * * * *